US007728015B2

(12) United States Patent
Barak

(10) Patent No.: US 7,728,015 B2
(45) Date of Patent: Jun. 1, 2010

(54) COMPOSITIONS FOR WEIGHT MANAGEMENT

(75) Inventor: Nir Barak, Tel-Aviv (IL)

(73) Assignee: Mor Research Applications Ltd., Tel-Aviv (IL)

( * ) Notice: Subject to any disclaimer, the term of this patent is extended or adjusted under 35 U.S.C. 154(b) by 103 days.

(21) Appl. No.: 11/363,332

(22) Filed: Feb. 28, 2006

(65) Prior Publication Data

US 2006/0148787 A1    Jul. 6, 2006

Related U.S. Application Data

(63) Continuation-in-part of application No. 11/283,865, filed on Nov. 22, 2005, and a continuation-in-part of application No. 11/283,928, filed on Nov. 22, 2005, each which is a continuation-in-part of application No. PCT/IL2005/000440, filed on Apr. 21, 2005.

(60) Provisional application No. 60/670,290, filed on Apr. 12, 2005.

(30) Foreign Application Priority Data

Apr. 22, 2004    (IL)    ..................... 161595

(51) Int. Cl.
A61K 31/4402    (2006.01)
(52) U.S. Cl. ................................... 514/357
(58) Field of Classification Search ........................ None
See application file for complete search history.

(56) References Cited

U.S. PATENT DOCUMENTS

| 4,159,332 | A | 6/1979 | Bollenbacher |
| 6,620,942 | B2 | 9/2003 | Yeh et al. |
| 2003/0162824 | A1* | 8/2003 | Krul ..................... 514/406 |
| 2006/0073217 | A1 | 4/2006 | Barak |
| 2008/0003306 | A1 | 1/2008 | Barak |
| 2008/0004254 | A1 | 1/2008 | Barak |
| 2008/0004322 | A1 | 1/2008 | Barak |
| 2008/0004324 | A1 | 1/2008 | Barak |
| 2008/0051439 | A1 | 2/2008 | Barak |
| 2008/0051440 | A1 | 2/2008 | Barak |

FOREIGN PATENT DOCUMENTS

| WO | WO 00/38725 | 7/2000 |
| WO | WO 00/53162 | 9/2000 |
| WO | WO 02/087556 | 11/2002 |
| WO | WO 2004/024094 | 3/2004 |

OTHER PUBLICATIONS

Gheorghiu et al., Am. J. Psychiatry, 156:11 (Nov. 1999), p. 1836.*
Rossi et al., Physiology & Behavior, 66(3), pp. 517-521 (1999).*
Leak et al., "Patients on Atypical Antipsychotic Drugs: Another High-Risk Groupfor Type 2 Diabetes", Diabetes Care, 26(11): 3202-3203, 2003.
Garrow, "Does Cimetidine Cause Weight Loss?", British Medical Journal, 306: 1084, 1994.
Rasmussen et al. "Cimetidine Suspension as Adjuvant to Energy Restricted Diet in Treating Obesity", British Medical Journal, 306: 1093-1096,1993.
Stoe-Birketvedt "Effect of Cimetidine Suspension on Appetite and Weight in Overweight Subjects", British Medical Journal, 306: 1091-1093, 1993.
Merck "Obesity", The Merck Manual of Diagnosis and Therapy, 17th Ed., p. 58-60, 1999.
Ito et al. "Toxicological and Teratological Studies on N-Methyl-N-β-(2-Pyridyl)-Ethylamine (Betahistine)", Oyo Yakuri, 2(4): 344-348, 1968.
Fossati et al. "Binding Affinity Profile of Betahistine and Its Metabolites for Central Histamine Receptors of Rodents", Pharmacological Research, 43(4): 389-392, 2001.
Malmlöf et al. "Influence of a Selective Histamine H3 Receptor Antagonist on Hypothalamic Neural Activity, Food Intake and Body Weight", International Journal of Obesity, p. 1-11, 2005.
Itoh et al. "Thioperamide, A Histamine H3 Receptor Antagonist, Powerfully Suppresses Peptide YY-Induced Food Intake in Rats", Biological Psychiatry, 45: 475-481, 1999.
Hagan "Peptide YY: A Key Mediator of Orexigenic Behavior", Peptides, 23: 377-382, 2002.
Poyurovsky et al. "The Effect of Betahistine, A Histamine H1 Receptor Antagonist/H3 Antagonist, on Olanzapine-Induce Weight Gain in First-Episode Schizophrenia Patients", International Clinical Psychopharmacology, 20: 101-103, 2005.
Kasaoka et al. "Histidine Supplementation Suppresses Food Intake and Fat Accumulation in Rats", Nutrition, 20: 991-996, 2004.
Baptista et al. "Drug Induced Weight Gain, An Impediment to Successful Pharmacotherapy: Focus on Antipsychotics", Current Drug Targets, 5: 279-299, 2004.
Kane et al. "Metabolic Effects of Treatment With Atypical Antipsychotics", Journal of Clinical Psychiatry, 65(11): 1447-1455, 2004.
Lieberman III "Metabolic Changes Associated With Antipsychotic Use", Primary Care Companion—Journal of Clinical Psychiatry, 6(Suppl.2): 8-13, 2004.
Newcomer "Second-Generation (Atypical) Antipsychotics and Metabolic Effects", CNS Drugs, 19(Suppl.1): 1-93, 2005.
Lecklin et al. "Inhibition of Histamine Catabolism Suppresses Fat Intake But Not the Intake of Carbohydrates and Protein", Inflammation Research, 51(Suppl.1): S53-S54, 2002.
Rasmussen et al. "Preclinical Pharmacology of FMPD [6-Fluoro-10-[3-(2-Methozyethyl)-4-Methyl-Piperazin-1-Y1]-2-Methyl-4H-3-Thia-4,9-Diaza-Benzo[f]Azulene]: A Potential Novel Antipsychotic With Lower Histamine H1 Receptor Affinity Than Olanzapine", The Journal of Pharmacology and Experimental Therapeutics, 315(3): 1265-1277, 2005.
Wetterling "Bodyweight Gain with Atypical Antipsychotics", Drug Safety, 24(1): 59-73, 2001.
Orthen-Gambill "Antihistaminic Drugs Increase Feeding, While Histidine Suppresses Fedding in Rats", Pharmacology Biochemistry & Behavior, 31: 81-86, 1988.
Sakata et al. "Blockade of the histamine Hi-receptor in the rat ventromedial hypothalamus and feeding elicitation",Brain Research, 441: 403-407, 1988.

(Continued)

Primary Examiner—Phyllis G. Spivack

(57) ABSTRACT

Pharmaceutical compositions are disclosed comprising betahistine, or a salt thereof, and olanzapine in amounts effective to reduce the weight gain associated with olanzapine administration.

7 Claims, 4 Drawing Sheets
(2 of 4 Drawing Sheet(s) Filed in Color)

OTHER PUBLICATIONS

Wirshing et al. "Novel Antipsychotics: Comparison of Weight Gain Liabilities", Journal of Clinical Psychiatry 60(6): 358-363, 1999.
Wirshing et al. "Schizophrenia and Obesity: Impact of Antipsychotic Medications", Journal of Cliinical Psychiatry, 65(18): 13-26, 2004.
Lecklin et al. "Effects of Intracerebroventricularly Infused Histamine and Selective $H_1$ H 2 and $H_3$ Agonists on Food and Water Intake and Urine Flow in Wistar Rats 3", Brain Research, 793: 279-288, 1998.
Masaki et al. "The Hypothalamic H1 Receptor: a Novel Therapeutic Target for Disrupting Diurnal feeding Rhythm and obesity", TRENDS in Pharmacological Sciences,.27 (.5):279-285.
Masaki et al. "Central Infusion of Histamine Reduces Fat Accumulation and Upregulates UCP Family in Leptin-Resistant Obese Mice", Diabetes, 50: 379-384, 2001.
Yoshimatsu et al. "Histamine Neurons Down-Regulate ob Gene Expression in Rat White Adipose Tissue", Inflamm. res. 50, (Suppl 2): S72-S73, 2001.
Masaki et al. "Involvement of Hypothalamic Histamine H1 Receptor in the Regulation of Feeding Rhythm and Obesity", Diabetes, 53, 2250-2260, 2004.
Rossi et al. "Effect of the H1-Histamine Receptor Agonist Betahistine on Drinking and Eating Behavior in Pygmy Goats" Physiology & Behavior, vol. 66, No. 3, pp. 517-521, 1999.
Szelag et al. "Betahistine Inhibits food Intake in Rats", Polish Journal of Pharmacology, Pol. J. Pharmacol., 2001, 53:701-707.
Abramof Ness et al. "Drug-Induced Weight Gain", Drugs of Today, 41, 2005.
Navarro-Badenes et al. "Weight gain associated with cinnarizine", Ann Pharmacother. 26(7-8):928-30. Jul.-Aug. 1992. Abstract.
Albera et al. "Double-Blind, Randomized, Multicenter Study Comparing the Effect of Betahistine and Flunarizine on the Dizziness Handicap in Patients With Recurrent Vestibular Vertigo", Acta Otalaryngol, 123: 588-593, 2003.
Arrang et al. "Actions of Betahistine at Histamine Receptors in the Brain", European Journal of Pharmacology, 111: 73-84, 1985.
Attoub et al. "The H3 Receptor Is Involved in Cholecystokinin Inhibition of Food Intake in Rats", Life Sciences, 69: 469-478, 2001.
Barbarich et al. "An Open Trial of Olanzapine in Anorexia Nervosa", Journal of Clinical Psychiatry, 65(11): 1480-1482, 2004.
Barrett et al. "Consensus Development Conference on Antipsychotic Drugs and Obesity and Diabetes", Journal of Clinical Psychiatry, 65(2): 267-272, 2004.
Bjenning et al. "OCFR and CFR (6-33) Depress Food But Not Water Intake in the Obese Zucker Rat", International Journal of Obesity, 24(Suppl.2):S140-S141, 2000.
Bustillo et al. "Differential Effect of Clozapine on Weight: A Controlled Study", The American Journal of Psychiatry, 153(6): 817-819, 1996.
Gordon et al. "Evaluation of Betahistine for the Prevention of Seasickness: Effect on Vestibular Function, Psychomotor Performance and Efficacy at Sea", Journal of Vestibular Research, 13: 103-111, 2003.
Onderwater et al. "Cytotoxicity of a Series of Mono- and Di-Substituted Thiourea in Freshly Isolated Rat Hepatocytes: A Preliminary Structure-Toxicity Relationship Study", Toxicology, 125: 117-129, 1998.
Sakata et al. "Hypothalamic Neuronal Histamine: Implications of Its Homeostatic Control of Energy Metabolism", Nutrition, 13: 403-411, 1997.
Seifert et al. "Multiple Differences in Agonist and Antagonist Pharmacology Between Human and Guinea Pig Histmaine H1-Receptor", The Journal of Pharmacology and Experimental Therapeutics, 305(3): 1104-1115, 2003.
Seipel et al. "Rheoencephalographic and Other Studies of Betahsitine in Humans: 1. The Cerebral and Peripheral Circulatory Effects of Single Doses in Normal Subjects", The Journal of Clinical Pharmacology, p. 144-154, 1975.
Snyman et al. "The Influence of Betahistine on the Dynamics of the Cutaneous Hypersensitivity Reaction in Patients With Grass Pollen Allergy", Immunopharmacology, 30: 71-78, 1995.
Theisen et al. "Spectrum of Binge Eating Symptomatology in Patients Treated With Clozapine and Olanzapine", Journal of Neural Transmission, 110: 111-121, 2003.

Wirshing "Schizophrenia and Obesity: Impact of Antipsychotic Medications", Journal of Clinical Psychiatry, 65(Suppl. 18): 13-26, 2004.
Yoshimatsu et al. "Histidine Suppresses Food intake Through Its Conversion Into Neuronal Histamine", Experimental Biology and Medicine, 227(1): 63-68, 2002.
Leurs et al. "Therapeutic Potential of Histamine H3 Receptor Agonists and Antagonists",Trends in Pharmacological Sciences, TiPS, 19: 177-184, 1998.
Lean et al. "Patients on Atypical Antipsychotic Drugs: Another High-Risk Group for Type 2 Diabetes", Diabetes Care, 26(11): 3202-3203, 2003.
Machidori et al. "Zucker Obese Rats: Defect in Brain Histamine Control of Feeding", Brain Research, 590: 180-186, 1992.
McMahon et al. "Efficacy and Safety of Sibutramine in Obese White and African American Patients With Hypertension. A 1-Year, Double-Blind, Placebo-Controlled, Multicenter Trial", Archives of Internal Medicine, 160: 2185-2191, 2000.
Morimoto et al. "Brain Histamine and Feeding Behavior", Behavioural Brain Research, 124: 145-150, 2001.
Barak "Betahistine: What's New on the Agenda", Expert Opinion in Investigational Drugs, 17(5): 795-804, 2008. Abstract.
Center for Drug Evaluation Research "Tablets ZOCOR® (Simvastatin)", Merck & Co., Inc., CDER NDA, Package Insert, Application No. 19-766/S040, 16 P., Jun. 2001.
Deshmukh et al. "Managing Weight Gain as a Side Effect of Antidepressant Therapy", Cleveland Clinic Journal of Medicine, 70(7): 614-623, Jul. 2003.
Remington "Remington: The Science and Practice of Pharmacy", Pharmaceutical Sciences, 19th Ed., I: 806, 1792, 1985.
Solvay Pharmaceuticals "Betaserc 24mg. Betahistine Dihydroch Oride", Leaflet, Solvay Pharmaceuticals, 1 P., Mar. 2002.
Barak "Histamine, the Hypothalamus and Feeding Behaviour", Anti-Obesity Drugs, p. 6-10, Apr./May 2008.
Bryden et al. "Body Mass Index Increase of 58% Associated With Olanzapine", American Journal of Psychiatry, 156(11): 1833-1844, 1999. p. 1835, r-h Col.-p. 1836, r-h Col.
Kogoj et al. "Olanzapine Induced Neuroleptic Malignant Syndrome—A Case Review", Human Psychopharmacology, 18: 301-309, 2003. Abstract, Table 1.
Merck "New Antipsychotic Drugs", The Merck Manual of Diagnosis and Therapy, 17th Ed., Sec.15 ( Psychiatric Disorders), p. 1570, 1999.
Szelag et al. "Lack of the Influence of Betahistine Administered Intragastrically on Food Intake in Rats", Advances in Clinical and Experimental Medicine, 11(3): 293-300, 2002. Abstract.
Szelag et al. "The Influence of Betahistine, Administered Intragastrically, on Ethanol Intake and Preference in Rats", Advances in Clinical and Experimental Medicine, 12(5): 2003. Abstract.
Dolvay Pharmaceuticals "Betaserc. Betahistidine Dihydrochloride", Leaflet of Betascrc 8 mg and 16 mg Tablets, Solvay Pharmaceuticals, 1 P., Mar. 2002.
Examination Report Dated Aug. 21, 2009 From the Government of India, Patent Office Re.: Application No. 2547/CHENP/2006.
Office Action Dated Jun. 8, 2009 From the Israeli Patent Office Re.: Application No. 161595 and Its Translation Into English.
Clifton et al. "Monoamine Receptors in the Regulation of Feeding Behaviour and Energy Balance", CNS & Neurological Disorders—Drug Targets, 5: 293-312, 2006.
Hill "Distribution, Properties, and Functional Characteristics of Three Classes of Histamine Receptor", Pharmacological Reviews, 42(1): 45-83, 1990.
Højby Rasmussen et al. "Cimetidine Suspension as Adjuvant to Energy Restricted Diet in Treating Obesity", BMJ, 306: 1093-1096, Apr. 24, 1993.
Little et al. "Role of Cholecystokinin in Appetite Control and Body Weight Regulation", Obesity Reviews, 6: 297-306, 2005.
Münzberg et al. "Leptin Receptor Action and Mechanisms of Leptin Resistance", CMLS, Cellular and Molecular Life Sciences, 62: 642-652, 2005.
Poothullil "Recognition of Oral Sensory Satisfaction and Regulation of the Volume of Intake in Humans", Nutritional Neuroscience, 8(4): 245-250, Aug. 2005.

* cited by examiner

Figures 1a-b (Prior Art)
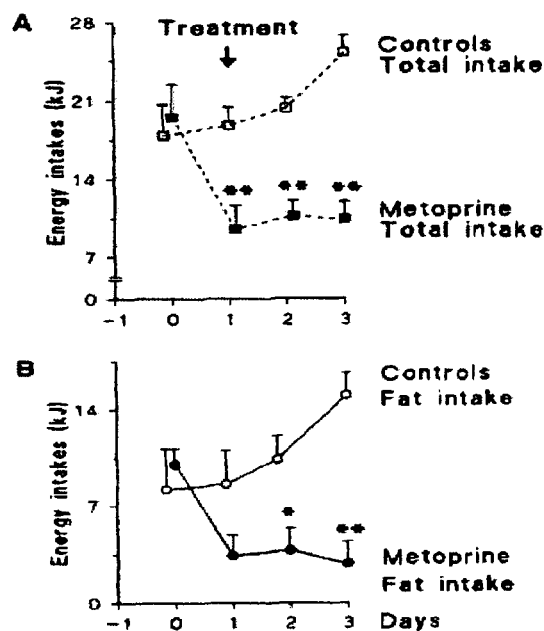
Figures 2a-b (Prior Art)
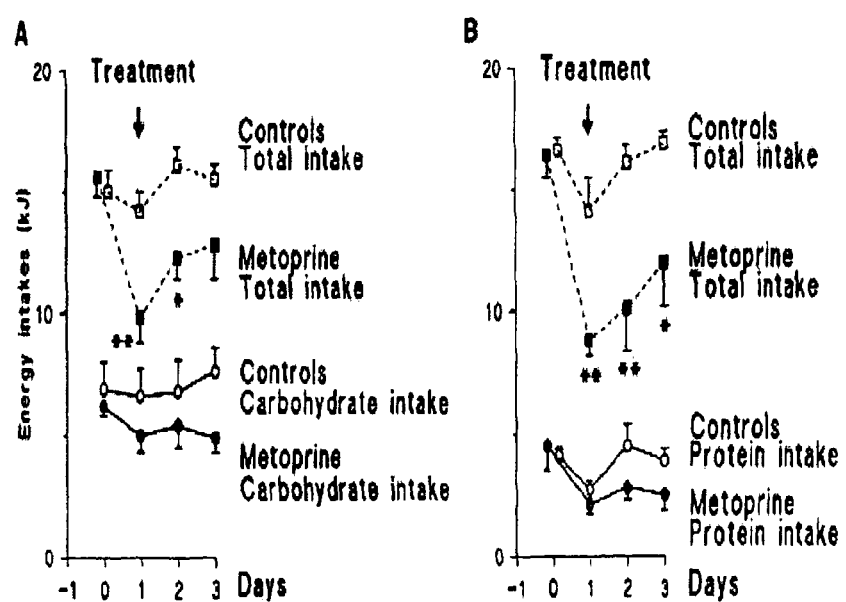

COMPOSITIONS FOR WEIGHT MANAGEMENT

RELATED APPLICATIONS

This application is a Continuation-In-Part (CIP) of U.S. patent application Ser. Nos. 11/283,865 and 11/283,928, co-filed on Nov. 22, 2005, each being a Continuation-In-Part (CIP) of PCT Patent Application No. PCT/IL2005/000440, filed on Apr. 21, 2005, which claims priority from U.S. Provisional Patent Application No. 60/670,290, filed on Apr. 12, 2005 and from Israel Patent Application No. 161595, filed on Apr. 22, 2004. The teachings of the above applications are hereby incorporated by reference as if fully set forth herein.

FIELD OF THE INVENTION

The present invention relates to novel compositions and methods for regulating food intake in human subjects and more particularly to compositions and methods for treating conditions in which weight management is beneficial. The present invention further relates to compositions and methods of reducing weight gain associated with drug treatment, smoking cessation and the like.

BACKGROUND OF THE INVENTION

Obesity is a chronic, complex, multi-factorial disease, involving social, cultural, genetic, physiological and psychological components, and is associated with substantially increased morbidity and mortality. Over-nutrition is attributed as the cause of about 400,000 deaths a year in the USA (Mokdad, 2004), and may considered to be an epidemic. Based on the body-mass index, defined as the ratio of weight and squared height, (ranging normally from 18.5 to 24.9), about one third of the adult population is overweight (an index of from 25 to 29.9), and more than one quarter is obese (index greater than 30) (*National Center for Health Statistics*, 2000). Environmental and behavioral changes brought about by economic development and modernization have been linked to the rise in global obesity. The environmental factors which foster the tendency toward obesity include lack of physical activity combined with high-calorie foods. The prevalence of overweight and obesity is increasing worldwide at an alarming rate in both developing and developed countries, in children and adults, men and women. The number of overweight and obese people has continued to increase since 1960, a trend that is not slowing down. Today, 64.5% of adult Americans—about 127 million—are categorized as being overweight or obese and nearly one-third (30.5%)—about 60 million—are obese, as reported in the National Health and Nutrition Examination Survey (NHANES) by the Centers for Disease Control and Prevention (CDC).

Obesity significantly increases the risk of illness from about thirty serious medical conditions and is associated with increases in deaths from all-causes. Among these are high blood pressure, diabetes, osteoarthritis, heart disease, stroke, gallbladder disease and cancer of the breast, prostate and colon (*National Task Force on the Prevention and Treatment of Obesity*, 2000). Furthermore, each year, obesity causes at least 300,000 excess deaths in the U.S., being the second leading cause of unnecessary deaths. Healthcare costs of American adults with obesity amount to approximately 100 billion dollars.

Weight gain has also been found to occur as a result of various factors, including, for example, use of certain drugs, cessation of smoking, and advent of a holiday season.

Drugs which are known to cause weight gain include antipsychotics, particularly atypical antipsychotics; antidepressants, particularly the tricyclic antidepressants; mood-stabilizers; calcium channel blockers; anti-convulsants; proton pump inhibitors; antidiabetic agents; antihypertensives; and hormones. Certain selective serotonin-reuptake inhibitors (SSRIs) also have an effect on weight gain, although other SSRIs, such as, sertraline, sibutramine and fluoxetine, often have the opposite effect, and are, in fact, used as appetite suppressants.

Weight gain associated with use of certain drugs may significantly affect patient compliance with the drug administration regime.

Certain drug categories, such as the SSRIs and tricyclic antidepressants, cause food cravings. Furthermore, such drugs may stimulate appetite by blocking of histamine receptors. For example, it has recently been shown that atypical antipsychotics, such as olanzapine and clozapine, as well as tricyclic and tetracylic antidepressants, such as amitriptyline and mirtazapine, respectively, which are potent $H_1$ antagonists, have a high propensity to induce weight gain (Wirshing, 1999).

Atypical antipsychotics have been frequently cited as causing a higher increase in weight gain than conventional antipsychotics (see, for example, Bustilllo, 1996). Weight gain was found to be greatest with clozapine, olanzapine, risperidone, and quetiapine, and less with aripiprazole and ziprasidone, and an additive effect on weight gain was found to occur in patients treated with antipsychotic medications and concomitantly with a drug from another class which may cause weight gain through a different mechanism, such as valproate (Kane, 2003). Weight gain with clozapine and olanzapine was found to persist for up to 30 weeks of treatment, and to be associated with a higher mean weight gain than for risperidone, haloperidol and sertindole (Wirshing, 2004). Risperidone-treated patients were found to gain weight for an initial 8-week period and then reach plateau level. Weight gain was also found to be more problematic for children and adolescents than for adults.

The mechanisms by which antipsychotic drugs cause weight gain are not clear. Antipsychotic drugs have multiple effects on neurotransmitter systems, which in turn have a range of effects on energy homeostasis. Most of the antipsychotics work through some degree of dopamine blockade (Wirshing, 2004), but modulation of the serotogenic, histaminergic, and adrenergic systems, all of which have potential impact on weight regulation, may also be involved. Most of the atypical antipsychotics work through a combination of receptor systems. Olanzapine and clozapine have the highest affinity for the $H_1$ receptor of all the atypical antipsychotics, and are also associated with the highest weight gain. A logarithmic relationship between H1 receptor affinity and weight gain has been demonstrated (Wirshing, 1999). In addition, many atypical antipsychotics exhibit activity at several serotonin receptor subtypes, including the $5-HT_{2C}$ subtype, which appears to mediate some effects on appetite. Olanzapine and clozapine both have high affinities for $5-HT_{2A}$, $5-HT_{2C}$, $H_1$-histaminergic, and $M_1$-muscarinic receptors. Clozapine also has high affinity for $\alpha_1$-adrenergic receptors. Ziprasidone, which is associated with minimal weight gain, has more serotogenic and less adrenergic, histaminic and muscarinic receptor affinity. Quetiapine has relatively high affinity for histamine receptors; risperidone has modest $H_1$ affinity, but notable affinity for $5-HT_{2A}$ and $5-HT_{2C}$ receptors. There are also endocrine effects of atypical antipsychotics, which presumably also play a role in weight gain.

A dual effect of the atypical antipsychotics in weight gain has been proposed: one, appetite stimulation by a direct effect on the brain, that may be observable in the short term; and second, a delayed endocrine/metabolic dysfunction that promotes fat deposition (Baptista, 2004). Involvement of the cytokine peptides leptin and tumor necrosis factor (TNF)-α in anti-psychotic-induced weight gain has also been suggested.

The use of atypical antipsychotics has also been found to place patients at risk for various metabolic disorders, including metabolic syndrome, which results in weight gain, as well as in hypertriglyceridemia, and in increased insulin, glucose, and low-density lipoprotein cholesterol levels (Lieberman, 2004). According to a recent review (Newcomer, 2005), clozapine and olanzapine treatment are associated with an increased risk of diabetes mellitus and dyslipidemia. A smaller effect is observed with risperidone and quetiapine. In general, it appears from the rank order of risk of diabetes and dyslipidemia observed for the atypical antipsychotics, that the risk is related to the differing weight gain liabilities of the drugs. It is suggested that the increased incidence of diabetes in patients receiving antipsychotics is not due purely to weight gain, since patients can develop diabetes without significant weight gain, and diabetes usually improves rapidly when the antipsychotic is withdrawn (Koller, 2001; Koller, 2002). The mechanisms leading to diabetes can include the drug induced weight gain, but there is also evidence of a direct metabolic effect. This may be related to antagonism at the 5-$HT_2$ or histamine $H_1$ receptors or to an elevation of serum leptin beyond that induced by increased body weight alone (Lean, 2003).

Dyslipidemia is most often associated with clozapine and olanzapine, and is primarily seen as an increase in triglyceride levels, but may also manifest as increased total cholesterol, LDL-cholesterol and decreased HDL-cholesterol (Barrett, 2004).

The use of atypical antipsychotics have also been associated with an increase in eating disorders, such as binge eating disorder, and bulimia nervosa (Theisen, 2003), which may be a secondary effect of the weight gain associated with these medicaments, resulting in reduced self esteem and repeated unsuccessful dietary trials.

Weight gain commonly occurs also as a result of cessation of smoking. This may be due to the fact that smoking burns calories, artificially elevates heart rate and increases metabolism. Upon cessation of smoking, the subject has to readjust to a lower metabolic rate.

Furthermore, nicotine is an appetite suppressant. Nicotine stimulates release of adrenaline, which acts upon the liver to step-up the breakdown of glycogen so that more glucose will be liberated into the blood. Nicotine also affects release of insulin, which controls glucose levels in the blood. Hence, nicotine causes slight hyperglycemia, and as a result, the body and brain may slow down the hormones and other signals that trigger feelings of hunger.

In addition, a subject suffering from nicotine withdrawal may turn to food for emotional comfort. Also, since smoking dulls the taste buds, food begins to taste better to new non-smokers, which can lead to increased food intake. Weight gain may also be caused by drugs prescribed to assist in smoking cessation. Anti-smoking medications include Zyban™ (bupropion hydrochloride).

Weight gain frequently also occurs during a holiday season, when the subject may have more opportunity to over-indulge in food, due to increased leisure time, increased availability of food, reduced exercise etc., or due to increased participation in meals in a social context. Such weight gain is greater during holidays, such as religious or national holidays, which are associated with consumption of specific foods or festive meals. Examples of such holidays include Thanksgiving, Christmas, and Passover.

There are several different treatment options for management of weight, including: dietary therapy, physical activity, behavior therapy, drug therapy and surgery. For the majority of overweight and obese people, who find they are unable to change their lifestyle, drug therapy is the most favorable and applicable option. Although hundreds of millions of people are seeking drug therapy for the treatment of obesity, current drug therapies do not meet this need due to their undesired side effects and limited efficacy.

Medications for the treatment of obesity are currently approved for use in adults with a body-mass index of 30 or higher, or with a body-mass index of 27 or higher who have obesity-related medical problems (*Physicians' Desk Reference*, 2001). Approximately 10 percents of women and 3 percents of men with a body-mass index of 30 or higher reportedly use weight-loss medications (Serdula, 1999).

Medications currently approved for weight loss in the United States fall into two categories: those that decrease food intake by reducing appetite or increasing satiety (appetite suppressants), and those that decrease nutrient absorption. A potentially third category, medications increasing energy expenditure, such as ephedrine, is not currently approved for treating obesity in the United States.

The only FDA-approved medication for obesity that reduces nutrient absorption is orlistat (Xenical™), which acts by binding to gastrointestinal lipases in the lumen of the gut, preventing hydrolysis of dietary fat into absorbable free fatty acids and monoacylglycerols.

Most appetite suppressants work primarily by increasing the availability of anorexigenic neurotransmitters—notably norepinephrine, serotonin, dopamine, or some combination of these neurotransmitters—in the central nervous system. Noradrenergic drugs available in the United States include phentermine, diethylpropion, phendimetrazine, and benzphetamine. Some of these drugs are considered by the Drug Enforcement Administration (DEA) to have a potential for abuse. Amphetamines, which are considered to have a particularly high potential for abuse are no longer recommended for weight loss for this reason. The Food and Drug Administration (FDA) approves the medications for use of "a few weeks" only (generally presumed to be 12 weeks or less) for the treatment of obesity.

Side effects of noradrenergic medications include insomnia, dry mouth, constipation, euphoria, palpitations, and hypertension (*Physicians' Desk Reference*, 2001).

Serotonergic agents act by increasing the release of serotonin, inhibiting its reuptake, or both. Fenfluramine (Pondimin™) and dexfenfluramine (Redux™), medications that both stimulate serotonin release and inhibit its reuptake, were withdrawn from the market in the United States in 1997 because of associations with valvular heart disease and pulmonary hypertension. Some selective serotonin-reuptake inhibitors have induced weight loss in short-term studies, and fluoxetine (Prozac) has undergone considerable evaluation to determine its efficacy for weight loss (Goldstein, 1993). However, after initial weight loss, steady regain was observed in later stages of the treatment (*National Task Force on the Prevention and Treatment of Obesity*). Sertraline (Zoloft™), evaluated as an adjunct for weight maintenance after a very-low-calorie diet, showed a similar lack of long-term efficacy (Wadden, 1995). Sibutramine (Meridia™, Reductil™), an inhibitor of both norepinephrine reuptake and serotonin reuptake that also weakly inhibits dopamine reuptake, is approved by the FDA for weight loss and weight maintenance in conjunction with a reduction diet. Side effects of sibutramine include increased blood pressure and pulse frequency rate (McMahon, 2000).

Rimonabant (Sanofi), which is claimed to stop food cravings, represents a new class of drugs that inhibit the activity of the CB1 receptor. The CB1 receptor forms a part of the endocannabinoid system. The CB1 receptor has been found in the brain, fat cells and other parts of the body, and has been associated with regulating food intake and with tobacco dependency (Pi-Sunyer et al., 2004). The endocannabiniod system helps to regulate pleasure, relaxation, and pain tolerance. Little is currently known about the long-term effects of inhibition of this system. Further, neurologists point out that the endocannabiniod system helps to protect the brain under some circumstances (such as stroke and head injury,) such that brain damage in these circumstances might be worse in patients taking drugs that block the endocannabiniod system.

The Rimonabant drug is currently undergoing phase III clinical trials. Presently reported side effects associated therewith include anxiety, nausea and diarrhea.

Hence, although some of the currently approved medications show moderate effects and can help some patients in losing weight, there is a continuing need for efficacious treatment regimes and drugs for alleviating the serious and prevalent disorder—the weight excess.

Histamine, a potent bioactive substance that has been studied for nearly a century, is an aminergic neurotransmitter. Four histamine receptors have been identified: $H_1$, $H_2$, $H_3$, and $H_4$, leading to the discovery and therapeutic use of potent receptor antagonists. Activation of the $H_1$ receptor is associated with effects on smooth muscle and central neurons; activation of the $H_2$ receptor stimulates acid secretion in the stomach, while activation of the $H_3$ receptor results in a presynaptic autoregulatory effect.

Histamine has been implicated, among others, in the regulation of arousal state (Lin et al., 1990), locomotor activity (Clapham, 1994), cardiovascular control (Imamura, 1996), water intake (Lecklin, 1998), food intake (Leurs, 1998), and memory formation (Blandina, 1996). It has been suggested that histaminergic neural circuits arising in the tuberomammilary nucleus and projecting into the satiety centers of the hypothalamus participate in regulation of food intake. Histaminergic neurons project into hypothalamic centers known to participate in food intake i.e. the paraventricular nucleus and ventromedial hypothalamus, where the anorectic effect is thought to be mediated by postsynaptic histamine $H_1$ receptors. The density of this receptor, together with the $H_3$-receptor-mediated control of the intrasynaptic concentration of histamine, both seem to be crucial for the strength of the anorectic signal. Some studies have indicated that histamine may suppress appetite by acting on hypothalamic histaminergic neurons that participate in the regulation of food intake (Sakata, 1997; Bjenning, 2000; Sakata, 1995). Thus, it was reported that histamine injected intracerebroventricularly acts as an appetite suppressant, and that depletion of histamine stimulates feeding (Tuomisto, 1994). Changes in histaminergic tone in the CNS have been associated with genetic models of obesity (Machidori, 1992). In addition, intracerebroventricular injection of leptin has been correlated with changes in the turnover rate of hypothalamic neuronal histamine (Yoshimatsu, 1999). Since histamine is unable to cross the blood brain barrier, these effects would not be expected to be seen with systemic administration of histamine.

In both humans and rodents, treatment with an $H_1$ antagonist resulted in hyperphagia (Fukagawa, 1989), and administration of $H_3$ antagonists led to hypophagia (Attoub, 2001). The selective histamine $H_3$ receptor antagonist NNC 38-109 has been reported to increase hypothalamic histamine levels, in parallel with decreases in food intake and body weight, according to studies in intact HEK293 cells expressing human or rat histamine $H_3$ receptors (Malmof, 2005). The intrasynaptic concentration of histamine is primarily controlled by feedback signals from presynaptic histamine $H_3$ receptors that inhibit both the conversion of L-histadine to histamine and the release of histamine into the synaptic clefts. Thus, by reducing the inhibition using a selective histamine $H_3$ receptor antagonist, the synaptic concentration of histamine increases together with the signaling from the histamine H1 receptor, and food intake is consequently inhibited. However, the long-term effects of $H_3$ receptors on anorexigenic activities for body-weight homeostasis have not been documented because of the off-target activity (Leurs, 1995) and toxicity profile of $H_3$ inhibitors (Onderwater, 1998).

Betahistine (also known by its chemical names 2-[2-(methylamino)ethyl]pyridine and N-methyl-2-pyridineethaneamine) is an orally active histamine-like drug extensively used in the symptomatic treatment of vestibular disorders, mainly Menier's disease and vertigo (including vertigo in patients with migraine (Amelin, 2003), dizziness with recurrent vertigo (*Acta Otolaryngol.*, 2003), vertigo in patients with vascular and traumatic cerebral injuries (Gusev, 1998), and benign paroxysmal positional vertigo (Fujino, 1994)). Studies have shown that betahistine can be further utilized in the treatment of a variety of disorders, including the aftereffects of craniocerebral injury and vascular events (Odinak, 2005), preventing or reducing myocardial infraction after occurrence of coronary occlusion (U.S. Pat. No. 4,159,332), multiple sclerosis (Boika, 2002), cutaneous hypersensitivity in patients with grass pollen allergy (Synman, 1995), arteriosclerotic dementia (Seipel, 1977), acute deafness (Grahne, 1976), vertebral-basilar insufficiency (Botez, 1975), and seasickness (*J. Vestib. Res.* 2003).

Betahistine is a structural analog of histamine, in which the imidazole ring of the histamine is replaced by a pyridine ring. Betahistine is an $H_1$ receptor agonist, and has been found to exhibit an $H_1$-agonism activity of about 0.07 times that of histamine, and to cause hypotensive response, bronchoconstriction, and increased vasopermeability after parenteral administration. Receptor binding studies have also shown that betahistine is a potent $H_3$-receptor antagonist. Betahistine is able to cross the blood brain barrier and act centrally by enhancing histamine synthesis is tuberomammillary nuclei of the posterior hypothalamus. Adverse side effected associated with betahistine are typically minor and include skin rashes of various types, urticaria, and itching. Gastric upset, nausea, and headache have also been reported by some patients.

It has been found (Rossi et al., 1999) that high doses of betahistine, delivered intraperitoneally, increased water intake and decreased food intake in pygmy goats. This was suggested as being due to stimulation of both $H_1$ and $H_2$ receptors, since in addition to its known action as an $H_1$ receptor agonist, betahistine has been shown to act as a weak partial agonist of peripheral histamine $H_2$ receptors (Arrang et al., 1985). This idea is further supported by recent findings showing that the hypophagic effect of histamine was blocked by the $H_2$-receptor antagonist, cimetidine, in pygmy goats. These similarities in the hypophagic effects of histamine and betahistine suggest an involvement of $H_2$-receptors in the hypophagic effect of betahistine in pygmy goats. $H_2$-receptors are not, however, associated with weight change in humans (Rasmussen, 1993).

Szelag et al. (2001) found that betahistine, when given intraperitoneally, decreased food intake in rats, whereas this effect was not seen when betahistine was given intragastrically (Szelag, 2002). It was suggested that the effect of betahistine administration on food intake involves increasing histamine synthesis and release as a result of $H_3$ receptor inhibition. However, since activation of $H_2$ receptors is known to stimulate hydrochloric acid secretion (see, for example, Clayman, 1977), it was further suggested that the lack of the influence of betahistine on food intake after intragastrical administration may be due to the fact that betahistine increased hydrochloric acid release by activation of $H_2$ receptors, thereby abolishing the central anorectic activity of betahistine.

It was also suggested that the effects on $H_1$ receptors in humans may differ significantly from those in rats due to variations in circadian rhythm between the species. Therefore, it appears that the anorectic response of betahistine is dependent upon species and route of administration. Nevertheless, Szelag et al. fail to teach the effect of betahistine administered orally or by any other route of administration, on food intake in humans.

Lecklin et al. (2002) found that inhibition of histamine catabolism by intraperitoneal injection of metoprine, a histamine-N-methyltransferase inhibitor, resulted in suppressed daily energy intake and ingestion of fat in rats.

Pharmacokinetic studies showed that betahistine is transformed, mainly in the liver, to 2-(2-aminoethyl)-pyridine (AEP) and to 2-(2-hydroxyethyl)-pyridine (HEP), (Sternoson, 1974) whereas both betahistine and the metabolites bind to histamine receptors.

The cited references corroborate the complexity of appetite regulation, which includes, among other factors, species specificity and route of administration. It has further been found (Seifert et al., 2003) that multiple differences exist in agonist and antagonist pharmacology of histamine receptors between different species, such as humans and guinea pigs. The prior art does not teach or suggest the use of $H_1$ agonists for regulating food intake in humans. The prior art further does not teach or suggest the use of such $H_1$ agonists that have a pharmacological half life that permits an efficient treatment therewith. The prior art further does not teach or suggest the use of orally administered $H_1$ agonists for regulating food intake in humans.

There is thus a widely recognized need for and it would be highly advantageous to have histamine-related agents for regulation of food intake in humans and for reducing weight gain associated with e.g., drug treatment, devoid of the above limitations.

SUMMARY OF THE INVENTION

The present invention successfully addresses the shortcomings of the presently known methods for regulating food intake by providing such methods that utilize $H_1$ receptor agonists, which are highly efficient in humans, which have a pharmacological half life of at least 3 hours and which are devoid of the limitations of the currently known methods. The present invention further provides methods for reducing weight gain associated with external factors such as drug treatment, smoking cessation and the like.

According to one aspect of the present invention there is provided a method of treating a condition in which regulating a food intake in a human subject is beneficial, the method comprising administering to the subject a therapeutically effective amount of an $H_1$ agonist, which has a pharmacological half-life of at least 3 hours.

According to further features in preferred embodiments of the invention described below, the condition is selected from the group consisting of overeating, overweight, obesity, and a disorder caused or exacerbated thereby. The condition caused or exacerbated by the conditions according to this aspect of the present invention may be selected from the group consisting of a muscosceletal disorder, a cardiovascular disorder, a dermatological disorder, a sleep disorder, a metabolic condition, diabetes and a diabetes-related condition.

According to still further features in the described preferred embodiments, the condition is associated with high fat consumption.

According to still further features in the described preferred embodiments, the condition is associated with a psychological factor. The condition according to this aspect of the present invention optionally comprises binge eating disorder, night eating syndrome, obsessive eating, compulsive eating or bulimia.

According to still further features in the described preferred embodiments the condition is associated with a drug treatment. The drug may optionally consist of a steroid hormone or a psychoactive drug, as is detailed hereinbelow.

According to another aspect of the present invention, there is provided a method of improving a compliance of a human subject to caloric restriction, the method comprising administering to the subject a therapeutically effective amount of an $H_1$ agonist, which has a half-life of at least 3 hours.

According to still another aspect of the present invention, there is provided a method of reducing a desire of a human subject to consume fats, the method comprising administering to the subject a therapeutically effective amount of an $H_1$ agonist, which has a half-life of at least 3 hours.

According to yet another aspect of the present invention, there is provided a method of treating a condition associated with a metabolic derangement in a human subject, the method comprising administering to the subject a therapeutically effective amount of an $H_1$ agonist which has a half-life of at least 3 hours. The metabolic derangement may be, for example, dyslipidemia, such as hypercholesterolemia or lipemia.

As used herein, the term "metabolic derangement" refers to an imbalance in the level of one or more metabolites within a body. A common metabolic derangement is typically associated with an imbalance in the level of metabolites such as cholesterol, including LDL and HDL, triglycerides and the like.

According to still another aspect of the present invention, there is provided a method of reducing total cholesterol level in a human subject, the method comprising administering to the subject a therapeutically effective amount of an $H_1$ agonist which has a half-life of at least 3 hours.

According to still another aspect of the present invention, there is provided a method of reducing low-density lipoprotein (LDL) cholesterol or increasing high-density lipoprotein (HDL) cholesterol levels in a human subject, the method comprising administering to the subject a therapeutically effective amount of an $H_1$ agonist which has a half-life of at least 3 hours.

According to still another aspect of the present invention, there is provided a method of reducing triglyceride level in a human subject, the method comprising administering to the subject a therapeutically effective amount of an $H_1$ agonist which has a pharmacological half-life of at least 3 hours.

According to yet another aspect of the present invention there is provided a method of treating an eating disorder, the method comprising administering to the subject a therapeutically effective amount of an $H_1$ agonist, said $H_1$ agonist having a pharmacological half-life of at least 3 hours.

The eating disorder can be, for example, bulimia and binge eating disorder.

According to a further aspect of the present invention there is provided a method of preventing weight gain or reducing weight in a subject, the method comprising administering to the subject a therapeutically effective amount of an $H_1$ agonist, said $H_1$ agonist having a pharmacological half-life of at least 3 hours.

According to further features in preferred embodiments of the invention described below, weight gain reduced by the method of the present invention may be associated with a drug treatment.

The drug may be, for example, an antipsychotic. Examples of such antipsychotics include, without limitation, selective serotonin-reuptake inhibitors (such as fluvoxamine, escitalopram, citalopram, and paroxetine); monoamine oxidase inhibitors (such as isocarboxazid, phenelzine and tranylcypromine); conventional antipsychotics (such as haloperidol, molindone and thioridazine); and atypical antipsychotics (such as clozapine, olanzapine, risperidone, quetiapine, sertindole, aripiprazole and ziprasidone, or an antagonist of a $5\text{-}HT_{2A}$, $5\text{-}HT_{2C}$, $H_1$-histaminergic or $M_1$-muscarinic receptor).

Alternatively, the drug may be an antidepressant. Examples of such antidepressants include, without limitation, a tricyclic antidepressant (such as amitryptyline, amoxapine, clomipramine, desipramine, doxepin, inupramine, nortryptyline, protriptyline or trimipramine), a tetracyclic antidepressant (such as mirtazapine or maprotiline), a serotonin-norepinephrine reuptake inhibitor (such as venlafaxine or duloxetine); and additional antidepressants such as biproprion hydrochloride, mitrazapine, nefazadone and trazadone.

Also alternatively, the drug may be a mood-stabilizer (such as lithium); a calcium channel blocker (such as diltiazem, nicardipine, verapamil and nimopidipine); an anti-convulsant (such as carbamazepine, divalproex, lamotrigine, sodium valproate, valproic acid, and gabapentin); a proton pump inhibitor (such as omeprazole, esomeprazole, lansoprazole and pantoprazole); an antidiabetic agent (such as a sulfonylurea, including chlorpropamide, glipizide, glyburide, and glimepiride, a meglitinide, a biguanide, a thiazolidinedione, an alpha-glucosidase inhibitor, and insulin); an antihypertensive (such as an alpha-adrenergic blocker, including doxazocin, prazocin and terazosin; or a beta blocker, including acebutolol, atenolol, metoprolol, nadolol, pindolol and propanolol); or an anti-smoking medication.

Further alternatively, the drug may be a hormone, such as, for example, a steroid hormone. Non-limiting examples of such steroid hormones include a corticosteroid (such as a glucocorticoid, including prednisone and cortisol; and a mineralocorticoid, including aldosterone and fludrocortisone); and a sex steroid (such as an androgen, including testosterone and dehydroepiandrosterone; an estrogen, such as estradiol; and a progestagen, such as progesterone or progestin), or mixtures thereof. Thus, for example the sex steroid may comprise estrogen and progestagen, such as provided as an oral contraceptive formulation; or estrogen and progestin, such as used for hormone replacement therapy.

According to yet further features in preferred embodiments of the invention, weight gain reduced by the method of the present invention may be due to cessation of smoking.

According to still further features in preferred embodiments of the invention described below, weight gain reduced by the method of the present invention may occur during a holiday season.

According to further features in the described preferred embodiments, the pharmacological half-life of the $H_1$ agonist ranges from about 3 hours to about 12 hours, preferably from about 3 hours to about 8 hours, more preferably from about 3 hours to about 5 hours.

According to still further features in the described preferred embodiments, the $H_1$ agonist is further an $H_3$ antagonist.

According to still further features in the described preferred embodiments, the $H_1$ agonist is characterized by blood brain barrier permeability.

According to still further features in the described preferred embodiments, the $H_1$ agonist is selected from the group consisting of betahistine, a betahistine metabolite, a betahistine pharmaceutically acceptable salt, a betahistine prodrug, a betahistine derivative and any combination thereof. Preferably, the betahistine metabolite is 2-(2-aminoethyl)-pyridine or 2-(2-hydroxyethyl)-pyridine. Also preferably, the betahistine salt is betahistine dihydrochloride, betahistine mesilate, or betahistine trimebutine maleate. Also preferably, the betahistine derivative is selected from the group of compounds represented by the general formula I:

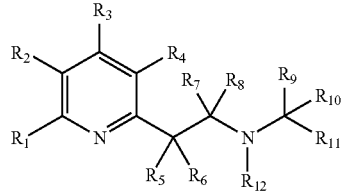

Formula I wherein each of $R_1$-$R_{12}$ is independently selected from the group consisting of hydrogen, alkyl, cycloalkyl and aryl.

According to still further features in the described preferred embodiments, in each of the methods described herein, administering is effected by a route selected from the group consisting of the oral, transdermal, intravenous, subcutaneous, intramuscular, intranasal, intraauricular, sublingual, rectal, transmucosal, intestinal, buccal, intramedullar, intrathecal, direct intraventricular, intraperitoneal, and intraocular routes. Preferably, administering is effected by the oral, transdermal, buccal, transmucosal, rectal or sublingual routes. More preferably, administering is effected by the oral, buccal or transdermal routes.

According to still further features in the described preferred embodiments, the therapeutically effective amount ranges from about 2 mg per day to about 96 mg per say, preferably from about 10 mg per day to about 50 mg per day.

According to still further features in the described preferred embodiments, administering is effected from about 1 to about 4 times per day, preferably, twice per day.

According to still further features in the described preferred embodiments, administering is effected according to the development of hunger of the subject.

According to still further features in the described preferred embodiments, administering is performed such that a decrease of the body weight of the subject that ranges from about 1 to about 5 percent is effected, without restricting the food intake of the subject. Preferably, such administering is performed such that no down-regulation of $H_1$ receptors is effected.

As used herein, the term "down-regulation" with regard to receptors refers to a decrease in the responsiveness of the receptor, or to a decrease in the number or density of receptors. Decreasing the responsiveness of a receptor also includes a complete shutdown of the receptor.

According to still further features in the described preferred embodiments, the $H_1$ agonist forms a part of a pharmaceutical composition, which further comprises a pharmaceutically acceptable carrier. Such a composition may optionally provide a slow release composition.

As used herein a "pharmaceutical composition" refers to a preparation of one or more of the active ingredients described herein, either compounds or physiologically acceptable salts thereof, with other chemical components such as traditional drugs, physiologically suitable carriers and excipients. Thus, pharmaceutical compositions, according to the present invention, can include, for example, the $H_1$ agonist described herein and an additional active ingredient, as is detailed herein.

For example, pharmaceutical compositions, according to the present invention, can include a therapeutically effective amount of the $H_1$ agonist described herein and a therapeutically effective amount of a drug associated with weight gain, as is detailed herein.

Such compositions can be used to treat a medical condition is which treatment with the drug is beneficial, as detailed herein, while reducing weight gain associated with the drug treatment, as discussed in detail hereinbelow.

Pharmaceutical compositions, according to the present invention, can include, for example, a therapeutically effective amount of the $H_1$ agonist described herein and a therapeutically effective amount of an agent for treating a metabolic derangement, as is detailed herein.

Such pharmaceutical compositions can be used in the treatment of conditions associated with high fat consumption, such as dyslipidemia, and hypercholesterolemia, for reducing total cholesterol level in a human subject, for reducing low-density lipoprotein cholesterol and increasing high-density lipoprotein cholesterol levels in a human subject and/or for reducing triglyceride level in a human subject.

According to still further features in the described preferred embodiments, each of the methods described herein further comprises administering to the subject a therapeutically effective amount of an additional active agent such as, for example, a weight control agent. The weight control agent may be, for example, an appetite suppressant. Representative examples of suitable appetite suppressants include, without limitation, noradrenergic agents, serotonergic agents, dopamingergic agents, endocannabinoid receptor blockers, or combinations thereof.

According to still further features in the described preferred embodiments, the additional active agent may be a non-steroidal anti-inflammatory drug, a muscle relaxant, an antigout agent, an immunosuppressant, a drug affecting bone mineralization, an angiotensin-converting enzyme inhibitor, an antiarrhythmic drug, an anticoagulant, an antiplatelet, a thrombolytic, a beta-adrenergic blocking drug, a centrally acting drug, a digitalis drug, a nitrate, a peripheral adrenergic antagonist, a vasodilator, an acne medication, an antipruretic agent, an anti-psoriasis agent, an anti-eczema agent, a hypnotic, an anti-histamine, a PPAR-gamma antagonist, insulin, a fibrate, an HMG-CoA reductase inhibitor, a bile acid sequestrant, a cholesterol absorption inhibitor, nicotinic acid, a derivative, analog and metabolite thereof, and any mixture thereof.

According to still further features in the described preferred embodiments, the additional active agent may be a nutritional supplement. An example of such a nutritional supplement is Histidine (Kasaoka S. *Nutrition* 20:991-996 (2004).

According to still further features in the described preferred embodiments, the methods described herein are used for inducing weight loss. Alternatively, these methods are used for maintaining weight loss or inhibiting a weight gain after or during a weight reducing diet. Further alternatively, these methods are used for preventing weight gain in a subject having a condition associated with weight gain.

In each of the methods described herein, the $H_1$ agonist is preferably not used for treating patients also having a medical condition that has previously been described as treatable by such an agonist.

Thus, in each of the various aspects of the present invention, the subjects treated by any of the methods described herein are preferably subjects that do not also suffer from a condition that has already been described in the art as treatable by the $H_1$ agonist described herein. Such conditions include, for example, Menier's disease, vertigo, seasickness, the after-effects of craniocerebral injury and vascular events, myocardial infraction after occurrence of coronary occlusion, multiple sclerosis, cutaneous hypersensitivity in patients with grass pollen allergy, arteriosclerotic dementia, acute deafness, and vertebral-basilar insufficiency.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or the appearance of clinical or aesthetical symptoms of a condition.

As used herein the term "regulating" with regard to food intake refers to controlling or adjusting the food intake to a desired level.

The term "comprising" means that other steps and ingredients that do not affect the final result can be added. This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

The term "therapeutically effective amount" or "pharmaceutically effective amount" denotes that dose of an active ingredient or a composition comprising the active ingredient that will provide the therapeutic effect for which the active ingredient is indicated.

As used herein, the term "agonist" describes a substance that is capable of binding to a receptor on a cell and thereby initiating a physiological activity or pathway. The phrases "$H_1$-receptor agonist" and "$H_1$ agonist" are used herein interchangeably.

As used herein, the term "antagonist" describes a substance that acts within the body to reduce the physiological activity of another substance.

As used herein, the phrase "pharmacological half-life" describes the time required for half the quantity of a drug or other substance deposited in a living organism to be metabolized or eliminated from the plasma by normal biological processes. This phrase is also referred to herein interchangeable as "half life".

As used herein, the term "pharmaceutically acceptable" means approved by a regulatory agency of the Federal or a state government or listed in the U.S. Pharmacopeia or other generally recognized pharmacopeia for use in animals, and more particularly in humans. Herein, the phrases "physiologically suitable carrier" and "pharmaceutically acceptable carrier" are interchangeably used and refer to an approved carrier or a diluent that does not cause significant irritation to an organism and does not abrogate the biological activity and properties of the administered conjugate.

As used herein, the term "carrier" refers to a diluent, adjuvant, excipient, or vehicle with which the therapeutic is administered.

Herein the term "excipient" refers to an inert substance added to a pharmaceutical composition to further facilitate processes and administration of the active ingredients.

As used herein, the singular form "a," "an," and "the" include plural references unless the context clearly dictates otherwise. For example, the term "a compound" or "at least one compound" may include a plurality of compounds, including mixtures thereof.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

BRIEF DESCRIPTION OF THE DRAWINGS

The file of this patent contains at least one drawing executed in color photograph. Copies of this patent with color photograph(s) will be provided by the Patent and Trademark Office upon request and payment of necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 3:
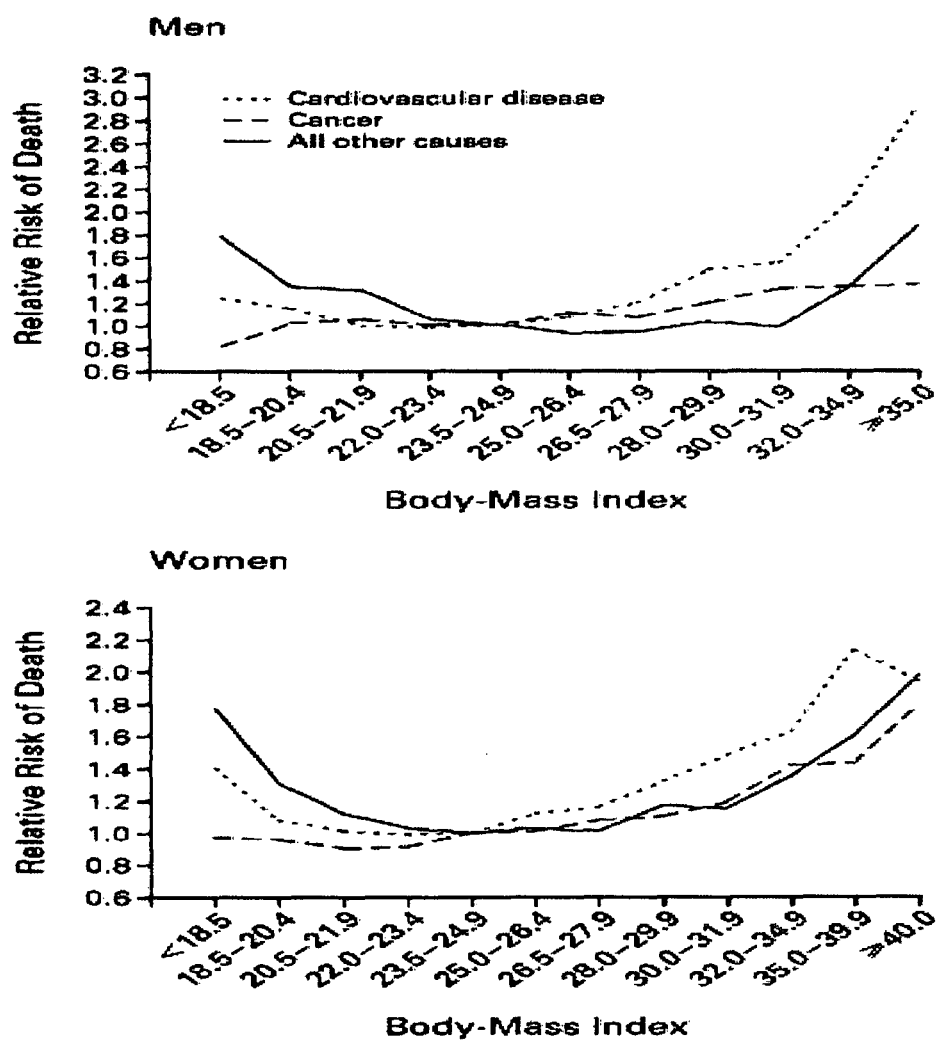
Figure 4:
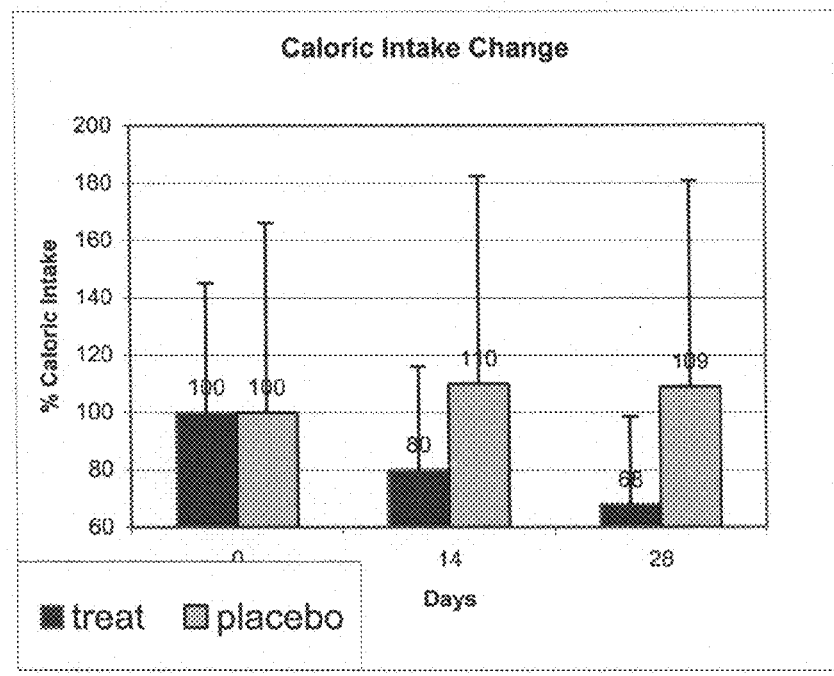
Figure 5:
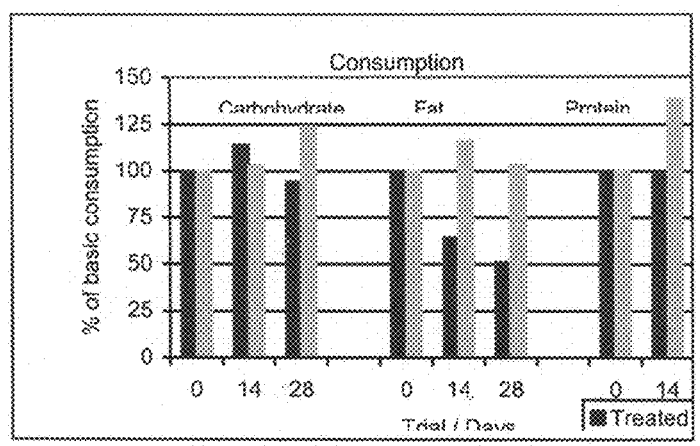
Figure 6:
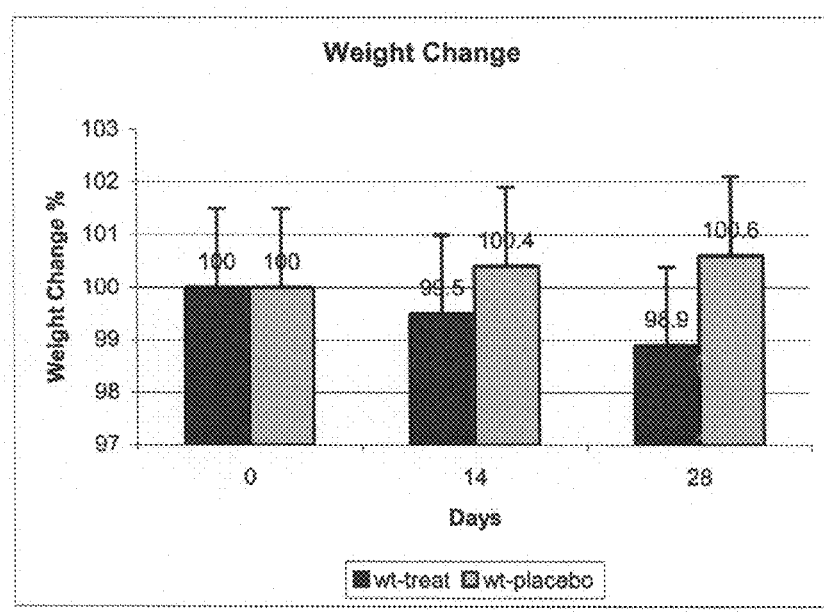

FIGS. 1(a-b) present results obtained in prior art studies, demonstrating the effect of Metoprine treatment on the total caloric intake (FIG. 1a) and the fat intake (FIG. 1b) in rats;

FIGS. 2(a-b) present results obtained in prior art studies, demonstrating the effect of Metoprine treatment on the total caloric intake, compared with the carbohydrate intake (FIG. 2a) and the protein intake (FIG. 1b) in rats;

FIG. 3 presents plots demonstrating the effect of overweight (expressed as the body mask index) on the relative risk of death from cardiovascular disease (dotted line), cancer (dashed line) and other causes in men (upper plots) and women (bottom plots);

FIG. 4 is a bar graph presenting the effect of oral administration of betahistine (blue bars) and a placebo (yellow bars) on the total caloric intake of humans following 14 days and 28 days of treatment;

FIG. 5 is a bar graph presenting the effect of oral administration of betahistine (blue bars) and a placebo (yellow bars) on the fat, carbohydrate and protein intake of humans following 14 days and 28 days of treatment; and FIG. 6 is a bar graph presenting the effect of oral administration of betahistine (blue bars) and a placebo (yellow bars) on the weight change in humans following 14 days and 28 days of treatment.

DETAILED DESCRIPTION OF THE INVENTION

The present invention is of novel methods for regulating food intake in a human subject; for improving a compliance of a human subject to caloric restriction; and for reducing a desire of a human subject to consume fats, all of which utilize $H_1$-receptor agonists that have a pharmacological half-life that allows an efficient treatment regime thereof. The present invention further provides a method for reducing weight gain in a human subject, by administration of $H_1$-receptor agonists that have a pharmacological half-life that allows an efficient treatment regime thereof.

The principles and operation of the compositions and methods according to the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

As is described hereinabove, many of the presently used appetite suppressants are known to have a potential for abuse. Furthermore, these appetite suppressants are associated with various side effects, ranging from insomnia, dry mouth, constipation, euphoria, palpitations and hypertension, to valvular heart disease and pulmonary hypertension. In addition, many of these agents have been found to show a lack of long-term efficacy, with steady weight-gain occurring after initial weight loss.

As is further described hereinabove, studies have shown a relationship between histamine and regulation of food intake. Thus, for example, as shown in FIG. 1, inhibition of histamine catabolism by the histamine N-methyltransferase inhibitor, metoprine, which is typically utilized as a cytotoxic, anticancer agent, has been shown to suppress total food intake and ingestion of fat by rats (Lecklin et al., 2002). Treatment had no marked effect on intakes of carbohydrates or protein, as shown in FIG. 2, indicating that an increase in the brain histamine content may reduce specifically "fat-appetite", namely, the desire to specifically ingest fats, as opposed to other food types.

Systemic administration of histamine, however, is extremely inefficient in its centrally mediated anti-obesity action because exogenous histamine poorly penetrates the blood brain barrier. Histamine has therefore been administered as an appetite suppressant hitherto by intracerebroventicular injection. Similarly, systemic administration of histamine would be expected to have little affect on the desire of a human subject to consume fats.

Furthermore, histamine has a pharmacological half-life of only a few minutes. Therefore, the duration of action of the drug is very short, and it would need to be administered frequently in order to build up and maintain a high enough concentration in the blood to be therapeutically effective. A drug having a longer half life would therefore require less frequent administration, which may lead to increased patient compliance with the dosing regime. This may also result in fewer side effects, as peaks and troughs of the level of the drug in the bloodstream of the patient may be decreased, leading to a more even drug level in the blood over a period of time.

While several studies have suggested a role for $H_1$-receptor agonists other than histamine in regulating food intake, none of these studies has established a direct effect of such agonists on food intake in humans.

The present inventors have now surprisingly found that certain $H_1$-agonists, which are characterized by relatively long half-life, particularly as compared with histamine, can be efficiently utilized for regulating food intake in humans. More specifically, it was found that betahistine, a presently known and approved drug for treating Menier's disease and associated conditions, and which has a half-life of about 3.5 hours, efficiently affects food intake and caloric intake and reduces weight, as well as fat consumption, in obese female subjects. As is exemplified in the Examples section that follows, in a randomized placebo controlled double-blinded study, it was found that betahistine hydrochloride decreased appetite, increase satiety lowered food intake and particularly affected fat consumption.

It is therefore demonstrated herein that the administration of an $H_1$ receptor agonist that has a pharmacological half life that permits reasonable and efficient treatment therewith (e.g., of at least 3 hour) can be beneficially used for regulating food intake and caloric intake in a human subject and hence for treating medical and psychological conditions associated with overweight. Without being bound to any particular theory, it is assumed that betahistine, as well as other $H_1$ receptor agonists, decrease food intake by a different mode of action than the currently used anti-obesity medications.

Thus, according to one aspect of the present invention there is provided a method of treating of a condition in which regulating a food intake in a human subject is beneficial, which is effected by administering to the subject a therapeutically effective amount of an $H_1$ agonist that has a pharmacological half-life of at least 3 hours.

It should be noted that as used herein the term "treatment" also includes amelioration or alleviation of a pathological condition and/or one or more symptoms thereof, curing such a condition.

The pharmacological half-life of the $H_1$ agonist utilized in this and other aspects of the present invention preferably ranges from about 3 hours to about 12 hours, more preferably from about 3 hours to about 8 hours, and even more preferably from about 3 hours to about 5 hours. Such a pharmacological half life is highly advantageous since, as is discussed hereinabove, such a drug remains in the blood for longer periods than, for example, histamine, achieving steadier blood levels, and therefore fewer side effects. The $H_1$ agonist of the present invention therefore needs to be administered far less frequently than, for example, histamine, which has a half life of only about 2 minutes. Since, as is known in the art, 97% of a drug is eliminated after 5 half lives, the administration should be repeated at intervals of less than 5 half lives, and usually less, depending on various parameters, including the clearance rate and the initial concentration administered.

In clinical practice, the choice of the dosage interval usually represents a compromise between the desirability of minimizing the variations of effectiveness between doses and patient inconvenience from too frequent dosing, which results in poor compliance. Dosage regimes of one or two administrations per day are considered optimal.

Using a drug having a half life within the above cited range allows for selecting the administration times so as to ensure maximal effectiveness of the drug at times of day when the effect is most required, such as at known meal times, periods of the day at which the subject most commonly experiences significant levels of hunger, etc., and to be least effective at times of day when no effect is necessary, such as, for example, during periods when the subject is expected to be asleep.

Drugs having a very long half life have the disadvantage that once or twice daily administration is clearly not possible. Less than daily administration is associated with poor patient compliance, as the subject tends to forget the necessity to take a medication which is not part of his daily routine. For example, the histamine-N-methyltransferase inhibitor, metoprine, which, as discussed above, has been shown to decrease food intake in rats, both by intraperitoneal injection and by central infusion, has a half life of 216 hours. Furthermore, the issue of toxicity must be considered with drugs having such long half lives.

In addition, it is known that a prolonged presence of $H_1$ agonists may lead to downregulation of the $H_1$ receptor.

Downregulation of a particular receptor after continuous activation can result in decreased response to agonist administration, due to adaptive changes in the receptors that limit their subsequent responsiveness, or to decrease in the number or density of receptors. These receptor-specific changes include a rapid uncoupling of receptors from activation of their cognate G proteins, mediating functional desensitization; a rapid redistribution of receptors into relatively inaccessible compartments in the plasma membrane or inside the cell, variously referred to as sequestration, endocytosis, or internalization; with prolonged agonist exposure, termed down-regulation. Considerable progress has been made in recent years in identifying the receptor modifications involved in these changes (Krupnick et al., 1998), although many of the details of the molecular modifications and protein-protein interactions that are involved in bringing about these changes remain to be determined. Down-regulation of a receptor type may lead to desensitization or tolerance to the agonist for the receptor. It is therefore believed that use of an $H_1$ receptor agonist having a half-life of less than 12 hours, preferably less than 8 hours and more preferably less than 5 hours prevents continuous exposure of the receptor to the agonist, and thereby down-regulation of the receptor is avoided.

The $H_1$ agonist of the present invention is preferably also an $H_3$ antagonist. $H_3$ antagonists have been shown to have an effect on regulation of food intake. It has been suggested that the inhibition of $H_3$ receptor activity increases histamine release and synthesis. Histamine subsequently increases histaminergic neuron activity via $H_1$ receptors and in this way inhibit food intake. $H_3$ receptors are located not only on histaminergic neurons, but also nonhistaminergic neurons as heteroreceptors, and modulate the release of 5-HT and noradrenaline. Thus, the effects of $H_3$ ligands on food intake may express through other endogenous substances (Morimoto et al., 2001).

Also preferably, the $H_1$ agonist is characterized by blood brain barrier permeability, and therefore is able to cross the blood brain barrier and enter brain tissue, thereby acting on central $H_1$ and $H_3$ receptors. This enables the agonist to be administered by the systemic route, in contrast to, for example, histamine, which has very poor blood brain barrier permeability and has therefore previously been administered as an appetite suppressant by intracerebroventicular injection.

The $H_1$ agonist of the present invention can be administered as any pharmaceutically acceptable salt, such as, for example, dihydrochloride, mesilate, or trimebutine maleate. Alternatively, the drug can be administered as any metabolite, prodrug, or derivative, or combination thereof.

The phrase "pharmaceutically acceptable salt" refers to a charged species of the parent compound and its counter ion, which is typically used to modify the solubility characteristics of the parent compound and/or to reduce any significant irritation to an organism by the parent compound, while not abrogating the biological activity and properties of the administered compound.

The term "prodrug" refers to an agent, which is converted into the active compound (the active parent drug) in vivo. Prodrugs are typically useful for facilitating the administration of the parent drug. They may, for instance, be bioavailable by oral administration whereas the parent drug is not. The prodrug may also have improved solubility as compared with the parent drug in pharmaceutical compositions.

As used herein, the term "metabolite" describes the actual active moiety of the compound which is formed as a result of metabolitic processes that occur in vivo upon administration of the compound.

The term "derivative" describes the result of chemically altering, modifying or changing a compound or a portion thereof, such that it maintains its original functionality in at least one respect.

According to a preferred embodiment of the present invention the $H_1$ agonist is betahistine. Betahistine is a structural analog of histamine, which has been shown to have a binding affinity profile which is qualitatively close to that of histamine for both $H_1$ and $H_3$ receptors (Fossati et al., 2001). Furthermore, it is pharmacologically relevant, since pharmacokinetic data have shown that therapeutic dosages of betahistine in humans give plasma concentrations which fall in the same range as its affinities for $H_1$ and $H_3$ receptors. The pharmacological relevance of betahistine for $H_1$ receptors is further confirmed in vivo in animals and humans, attributable to the increased blood flow in microcirculation in the auditory and internal vestibular system (Meyer et al., 1974). Since betahistine has already been widely used for treating vertigo and other disorders, it has been tested and is approved for use in human medicine.

Betahistine is readily absorbed through the oral route and is converted to at least two metabolites, 2-(2-aminoethyl)-pyridine and 2-(2-hydroxyethyl)-pyridine. Betahistine has an elimination half life time of 3.5 hours, and most of the dose is excreted via the urine as metabolites. Hence, betahistine may be administered according to a convenient dosage regime, as discussed above.

The side effects associated with betahistine are minor, consisting mainly of skin rashes of various types, urticaria, itching, gastric upset, nausea, headache, and exacerbation of symptoms in patients with a history of peptic ulcer.

Betahistine can be utilized in this and other aspects of the present invention either per se or as a metabolite, a pharmaceutically acceptable salt, a prodrug or a derivative thereof.

Betahistine metabolites that can be efficiently used in the context of the present invention include, for example, 2-(2-aminoethyl)-pyridine and 2-(2-hydroxyethyl)-pyridine. As is further described in the art (see, for example, Fossati et al., 2001) these metabolites are also characterized by $H_1$-receptor agonist activity and therefore can also be utilized in the various aspects of the present invention.

Representative examples of betahistine pharmaceutically acceptable salts that can be efficiently used in the context of the present invention include, without limitation, betahistine hydrochloride, betahistine dihydrochloride, betahistine mesilate, and betahistine trimebutine maleate.

Betahistine derivatives that are suitable for use in the context of this and other aspects of the present invention include, for example, compounds having the general Formula I:

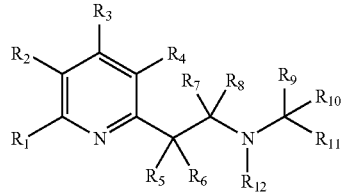

Formula I

In Formula I, each of $R_1$-$R_{12}$ is preferably independently selected from the group consisting of hydrogen, alkyl, cycloalkyl and aryl and any combination thereof.

Optionally, each of $R_1$-$R_{12}$ can also be selected from other substituents, as long as features such as the blood brain barrier permeability, the half life and the binding to the $H_1$-receptor of the compound are not adversely affected. Thus, each of $R_1$-$R_{12}$ can be further independently selected, for example, from alkenyl, alkynyl, alkoxy, aryloxy, hydroxy, thiohydroxy, thioalkoxy, thioaryloxy, halide, amino, nitro, cyano, carbonyl, C-carboxy, O-carboxy, C-carmabyl, N-carbamyl, sulfonyl, sulfinyl, sulfonamide, urea, thiourea, guanidine, guanyl, O-carbamyl, N-carbamyl, O-thiocarbamyl, N-thiocarbamyl, C-amido, N-amido, N-sulfonamido, and S-sulfonamido or, alternatively, at least two of $R_1$-$R_4$ and/or at least two of $R_5$-$R_{12}$ form at least one four-, five- or six-membered aromatic, heteroaromatic, alicyclic or heteroalicyclic ring.

It will be appreciated by one of skills in the art that the feasibility of each of the substituents ($R_1$-$R_{12}$) to be located at the indicated positions depends on the valency and chemical compatibility of the substituent, the substituted position and other substituents. Hence, the present invention is aimed at encompassing all the feasible substituents for any position.

As used herein, the term "alkyl" refers to a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 4 carbon atoms. The alkyl group may be substituted or unsubstituted.

A "cycloalkyl" group refers to an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or unsubstituted.

An "alkenyl" group refers to an alkyl group which consists of at least two carbon atoms and at least one carbon-carbon double bond.

An "alkynyl" group refers to an alkyl group which consists of at least two carbon atoms and at least one carbon-carbon triple bond.

An "aryl" group refers to an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted.

A "heteroaryl" group refers to a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine.

A "heteroalicyclic" group refers to a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. Representative examples are piperidine, piperazine, tetrahydrofurane, tetrahydropyrane, morpholino and the like.

A "hydroxy" group refers to an —OH group.

An "alkoxy" group refers to both an —O-alkyl and an —O-cycloalkyl group, as defined herein.

An "aryloxy" group refers to both an —O-aryl and an —O-heteroaryl group, as defined herein.

A "thiohydroxy" group refers to a —SH group.

A "thioalkoxy" group refers to both an —S-alkyl group, and an —S-cycloalkyl group, as defined herein.

A "thioaryloxy" group refers to both an —S-aryl and an —S-heteroaryl group, as defined herein.

A "carbonyl" group refers to a —C(=O)—R' group, where R' is hydrogen, alkyl, alkenyl, cycloalkyl, aryl, heteroaryl (bonded through a ring carbon) or heteroalicyclic (bonded through a ring carbon) as defined herein.

A "thiocarbonyl" group refers to a —C(=S)—R' group, where R' is as defined herein for R'.

A "C-carboxy" group refers to a —C(=O)—O—R' group, where R' is as defined herein.

An "O-carboxy" group refers to an R'C(=O)—O— group, where R' is as defined herein.

A "halide" group refers to fluorine, chlorine, bromine or iodine.

A "sulfinyl" group refers to an —S(=O)—R' group, where R' is as defined herein.

A "sulfonyl" group refers to an —S(=O)$_2$—R' group, where R' is as defined herein.

An "S-sulfonamido" group refers to a —S(=O)$_2$—NR'R" group, with R' is as defined herein and R" is defined for R'.

An "N-sulfonamido" group refers to an R'S(=O)$_2$—NR" group, where R' and R" are as defined herein.

An "O-carbamyl" group refers to an —OC(=O)—NR'R" group, where R' and R" are as defined herein.

An "N-carbamyl" group refers to an R"OC(=O)—NR'— group, where R' and R" are as defined herein.

An "O-thiocarbamyl" group refers to an —OC(=S)—NR'R" group, where R' and R" are as defined herein.

An "N-thiocarbamyl" group refers to an R"OC(=S)NR'— group, where R' and R" are as defined herein.

An "amino" group refers to an —NR'R" group where R' and R" are as defined herein.

A "C-amido" group refers to a —C(=O)—NR'R" group, where R' and R" are as defined herein.

An "N-amido" group refers to an R'C(=O)—NR" group, where R' and R" are as defined herein.

A "urea" group refers to an —NR'C(=O)—NR"R'" group, where R' and R" are as defined herein and R'" is defined as either R' or R".

A "guanidino" group refers to an —R'NC(=N)—NR"R'" group, where R', R" and R'" are as defined herein.

A "guanyl" group refers to an R'R"NC(=N)— group, where R' and R" are as defined herein.

A "nitro" group refers to an —NO$_2$ group.

A "cyano" group refers to a —C≡N group.

The term "phosphonyl" describes a —O—P(=O)(OR')(OR") group, with R' and R" as defined hereinabove.

The term "phosphinyl" describes a —PR'R" group, with R' and R" as defined hereinabove.

The term "thiourea" describes a —NR'C—(=S)—NR"R'" group, with R' and R" as defined hereinabove and R'" as defined herein for R' and R".

In any of the methods described herein, the H$_1$ agonist can be administered by any route selected from the oral, transdermal, intravenous, subcutaneous, intramuscular, intranasal, intraauricular, sublingual, rectal, transmucosal, intestinal, buccal, intramedullar, intrathecal, direct intraventricular, intraperitoneal, or intraocular routes. Preferably, the route of administration is selected from the oral, transdermal, buccal, transmucosal, rectal or sublingual routes. More preferably, the H$_1$ agonist is administered using the oral, buccal or transdermal route.

The H$_1$ agonist is optionally and preferably administered as a total dose of from about 2 mg to about 96 mg per day. More preferably, the total dose is from about 5 mg to about 50 mg per day, more preferably from about 10 mg to about 50 mg, more preferably from about 16 mg to about 48 mg and most preferably it is from about 24 mg to about 48 mg.

The H$_1$ agonist is preferably administered once or several times a day, for example from about 1 to about 4 times per day, and, more preferably, twice per day. Alternatively, the H$_1$ agonist may be administered according to the development of hunger of the subject.

As is demonstrated in the Examples section that follows, clinical studies have indicated that administering a 16 mg dose of betahistine twice a day for a month, without restricting their food intake, resulted in a significant weight loss, particularly as compared with a control group.

Hence, according to an embodiment of the present invention, a treatment regime is performed such that upon repetitious administration, a decrease of the body weight of the subject that ranges from about 1 to about 5 percent is effected, without restricting the food intake of the subject.

Since, as is discussed in detail hereinabove, constant presence of a H$_1$ agonist may result in substantial downregulation of the $H_1$ receptor, a more preferred treatment regime according to the present invention is performed such that such a decrease in a body weight is achieved without effecting downregulation of the $H_1$ receptor. Such a treatment regime can be designed by adjusting the dosing and the administration intervals to the half life of the selected H1 agonist.

The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1). Dosage amount and interval may be adjusted individually to provide plasma levels of the $H_1$ agonist which are sufficient to maintain the regulating effects.

When the $H_1$ agonist is betahistine, which is commercially available as tablets of 8 mg or 16 mg, the daily dosage range is from 24 to 48 mg, administered orally in divided doses. For example, the 8 mg tablet is administered as 1 to 2 tablets 3 times daily, and the 16 mg tablet is administered as 0.5 to 1 tablet 3 times daily.

The $H_1$ agonist of the present invention may optionally be administered in the form of a slow-release preparation, having a reduced rate of release of the active substance, in order to further increase patient convenience and compliance and optionally the efficiency of the active agent. The slower the rate of release, the less the blood concentrations fluctuate within a dosing interval. This enables higher doses to be given less frequently, while maintaining therapeutic concentrations over prolonged periods. Furthermore, slow-release preparations are beneficial in reducing potential side-effects of the active ingredient due to transiently high peak blood concentrations being reached soon after administration.

Slow release preparations typically include slow release biodegradable carriers. Slow release biodegradable carriers are well known in the art. These are materials that may form particles that may capture therein an active compound(s) and slowly degrade/dissolve under a suitable environment (e.g., aqueous, acidic, basic, etc.) and thereby degrade/dissolve in body fluids and release the active compound(s) therein. The particles are preferably nanoparticles (i.e., in the nanometer range, e.g., in the range of about 1 to about 500 nm in diameter, preferably about 50-200 nm in diameter, most preferably about 100 nm in diameter).

The rate at which a drug is released is generally dependent on the rate at which the dosage form disintegrates or dissolves. Disintegration greatly increases the drug's surface area in contact with GI fluids, thereby promoting drug dissolution and absorption. Disintegrants and other excipients (e.g., diluents, lubricants, surfactants, binders, dispersants) are often added during manufacture to facilitate these processes. Surfactants increase the dissolution rate by increasing the wettability, solubility, and dispersibility of the drug. Disintegration of solid forms may be retarded by excessive pressure applied during the tableting procedure or by special coatings applied to protect the tablet from the digestive processes of the gut. Hydrophobic lubricants (e.g., magnesium stearate) may bind to the active drug and reduce its bioavailability.

Dissolution rate determines the availability of the drug for absorption. When slower than absorption, dissolution becomes the rate-limiting step. Overall absorption can be controlled by manipulating the formulation. For example, reducing the particle size increases the drug's surface area, thus increasing the rate and extent of GI absorption of a drug whose absorption is normally limited by slow dissolution. Dissolution rate is affected by whether the drug is in salt, crystal, or hydrate form.

Oral slow-release forms are often designed to maintain therapeutic drug concentrations for greater than 12 hours. The absorption rate can be controlled by coating drug particles with wax or other water-insoluble material, by embedding the drug in a matrix from which it is released slowly during transit through the GI tract, or by complexing the drug with ion-exchange resins.

Thus, for example, a slow-release formulation in tablet form, may be based on the use of a hydrophilic polymer which swells in contact with gastrointestinal fluids, to form a gel, which creates a barrier that enrobes the tablet. The barrier limits physical exchanges between the inside of the tablet and the surrounding medium. As a consequence, intrusion of water towards the tablet matrix and diffusion of drug are slowed down, allowing a controlled slow release of the drug.

Various types of polymers may be used as a matrix for the slow-release of drugs, such as polyvinyl chloride, polyethylene polyamides, ethylcellulose, silicone, poly (hydroxyethyl methacrylate), other acrylic co-polymers, and polyvinylacetate-polyvinyl chloride copolymers.

Thus, a slow-release formulation for delivery of the $H_1$ agonist of the present invention provides for release over a period that ranges from about 2 hour to about 24 hours, preferably from about 4 hours to about 24 hours and hence, for release over a period of at least 4 hour, at least 5 hours, at least 6 hours, at least 7 hours, at least 8 hours, at least 9 hours, at least 10 hours, at least 11 hours, at least 12 hours, at least 13 hours, at least 14 hours, at least 15 hours, at least 16 hours, at least 17 hours, at least 18 hours, at least 19 hours, at least 20 hours, at least 21 hours, at least 22 hours, at least 23 hours, or at least 24 hours. Alternatively, such a slow-release formulation provides for release of the $H_1$ agonist over a period of more than 24 hours and up to 48 hours.

The method according to this aspect of the present invention can thus be efficiently used for treating any condition in which regulating food intake is beneficial. These include, for example, overeating, overweight, obesity, and disorders caused or exacerbated thereby.

Diseases caused by or exacerbated by these conditions include, for example, muscosceletal disorders (such as osteoarthritis, spine-related pains, etc.), cardiovascular disorders (such as hypertension, atherosclerosis, etc.), dermatological disorders (such as fungal and other infections), sleep disorder (such as snoring and obstructive sleep apnea), metabolic conditions (dyslipidemia, lipemia or hypercholesterolemia), diabetes and diabetes-related problems, as well as cancer (particularly breast, prostate and colon cancer). The effect of overweight, expressed by the body mass index, on the relative risk of death from various disorders caused or exacerbated thereby, is demonstrated in FIG. 3. As shown in FIG. 3, cardiovascular disease increases significantly in overweight subjects, both male and female, as compared to those within the normal body-mass index range (i.e. from 18.5 to 24.9). A further sharp increase is observed in subjects classified as obese (i.e. having body mass of greater than 30). Similarly, an increase in the relative risk of death from cancer is seen in overweight subjects, particularly in obese subjects, with a greater increase amongst females. The relative risk of death from other causes is seen to increase sharply in obese individuals.

Additional conditions that are treatable by the method according to this aspect of the present invention include, for example, conditions that are associated with a psychological factor, such as binge eating disorder, night eating syndrome, obsessive eating, compulsive eating and bulimia.

Bulimia is a psychological condition in which the subject engages in recurrent binge eating followed by intentionally doing one or more of the following in order to compensate for the intake of the food and prevent weight gain: vomiting; inappropriate use of laxatives, enemas, diuretics or other medication; excessive exercising; fasting. Some anorectics may demonstrate bulimic behaviors in their illness: binge-eating and purging themselves of food on a regular or infrequent basis at certain times during the course of their disease. Bulimia may occur without the serious weight loss which is symptomatic of anorexia. An increase in binge eating has been reported amongst patients receiving atypical antipsychotics (Theisen, 2003), apparently as a result of attempts to compensate for weight gain induced by the antipsychotic. The use of betahistine to avoid this weight gain may therefore be beneficial in preventing the resulting compensatory behavior which leads to bulimia. Furthermore, the reduction in appetite resulting from administration of betahistine further contributes to the prevention of the overeating/purging cycle which characterizes bulimia.

As is detailed hereinbelow, it has been suggested that the $H_1$ agonist described herein interferes with appetite-stimulating histaminergic activity of steroidal or anti-psychotic drugs.

Peptide YY (PYY) is a peptide with 36 amino acids that originates from the intestine. Studies have shown that elevated PYY levels were detected in patients suffering from eating disorders (Hagan, 2002). In addition, thioperamide, an $H_3$ antagonist, has been shown to block the ability of increased levels of PYY to increase food consumption (Itoh, 1999). Since $H_3$ antagonists increase neuronal histamine levels and since this increased histamine binds to $H_1$ receptors, the $H_1$ agonist described herein can be further efficiently used in treating such eating disorders via its histaminergic activity.

Hence, according to another aspect of the present invention there is provided a method of treating an eating disorder, and particularly bulimia. The method according to this aspect of the present invention is effected by administering to a subject suffering from an eating disorder such as bulimia a therapeutically effective amount of the $H_1$ agonist described herein.

The $H_1$ agonist described herein may be further utilized for at least reducing weight gain, and preferably weight gain caused by factors other than excessive food consumption.

Thus, according to a further aspect of the present invention, there is provided a method of reducing weight gain, which is effected by administering to the subject a therapeutically effective amount of an $H_1$ agonist that has a pharmacological half-life of at least 3 hours, as described hereinabove.

Such weight gain may be due to factors which include, for example, use of certain drugs, cessation of smoking, or due to a holiday season, as discussed hereinabove and is further detailed hereinbelow.

Thus, in one embodiment, the method according to this aspect of the present invention, can be implemented to reduce weight gain associated with drug treatment.

Presently, many drugs are known to cause weight gain. Representative examples include, without limitation, antipsychotics, antidepressants, mood-stabilizers, calcium channel blockers, anti-convulsants, proton pump inhibitors, antidiabetic agents, antihypertensives, hormones, and anti-smoking medications.

As is described in the art, the histaminergic system has been implicated in weight gain associated with steroid-induced and antipsychotic-induced weight gain (Poyurovsky et al., 2005). Poyurovsky et al. (2005) report that in a study conducted in three first-episode schizophrenia patients, treated with betahistine and olanzapine for 6 weeks, no weight gain was observed from week 2 to the end of the study, and that the mean weight gain in betahistine/olanzapine-treated patients was lower than that observed in olanzapine/placebo-treated patients (see, page 102, right column, Table 1 and the "Discussion" section therein). Hence, the $H_1$-receptor agonists of the present invention may be co-administered together with a drug treatment which is known to cause appetite stimulation and weight gain in humans due to its histaminergic activity. It is assumed that the $H_1$ agonist utilized herein interferes with appetite stimulating histaminergic activity of the steroidal or anti-psychotic drug mentioned above and thus prevents or reduces the weight gain caused by such drug treatment.

Representative examples of antipsychotic drugs associated with weight gain include, without limitation, selective serotonin-reuptake inhibitors (SSRIs) (such as fluvoxamine, escitalopram, citalopram, or paroxetine), monoamine oxidase inhibitors (such as isocarboxazid, phenelzine and tranylcypromine), conventional antipsychotics (such as haloperidol, molindone and thioridazine), and atypical antipsychotics, (such as clozapine, olanzapine, risperidone, quetiapine, sertindole, aripiprazole and ziprasidone. Particular examples of antipsychotic drugs associated with weight gain are those which are antagonists of serotonin receptors, including 5-$HT_{2A}$, and 5-$HT_{2C}$ subtypes, or of $H_1$-histaminergic, and $M_1$-muscarinic receptors. These include, for example, clozapine, olanzapine, risperidione and pirenzepine.

As discussed hereinabove, the mechanisms by which antipsychotic drugs cause weight gain are not clear, but appear to involve multiple effects on neurotransmitter systems, such as the serotogenic, histaminergic, and adrenergic systems.

Atypical antipsychotics, particularly clozapine, olanzapine, risperidone, and quietiapine, have been shown to cause a higher increase in weight gain than conventional antipsychotics. The effect of these antipsychotics may involve both appetite stimulation by a direct effect on the brain, and a delayed endocrine/metabolic dysfunction that promotes fat deposition. One study (Poyurovsky 2005) has identified an attenuating effect of betahistine on weight gain due to olanzapine, from week 2 to the end of the study. Since olanzapine is a potent $H_1$ antagonist, and betahistine was found not to interfere with the antipsychotic effect of olanzapine, it has been suggested that the antagonistic effect of betahistine on the presynaptic $H_3$ receptor may account for the weight gain attenuation.

Weight gain may also occur due to the use of hormones, particularly steroid hormones, such as corticosteroids or sex steroids. Corticosteroids include glucocorticoids, (for example, prednisone and cortisol), and mineralocorticoids (for example, aldosterone and fludrocortisone). Sex steroids include androgens (for example, testosterone and dehydroepiandrosterone), estrogens (such as estradiol), and progestagens, (for example, progesterone and progestin). Estrogens and progestagens are administered as oral contraceptives. Estrogen and progestin are administered as hormone replacement therapy for menopausal women.

Other drugs which may cause weight gain include antidepressants, including, for example, tricyclic antidepressants (such as amitryptyline, amoxapine, clomiprmine, desipramine, doxepin, imipramine, nortryptyline, protriptyline and trimipramine), tetracyclic antidepressants (such as mirtazapine and maprotiline), serotonin-norepinephrine reuptake inhibitors (such as venlafaxine and duloxetine), and other anti-depressants (such as biproprion hydrochloride, mitrazapine, nefazadone and trazadone); mood-stabilizers, such as lithium; calcium channel blockers (such as diltiazem, nicardipine, verapamil and nimopidipine); anti-convulsants (such as carbamazepine, divalproex, lamotrigine, sodium valproate, valproic acid, and gabapentin); proton pump inhibitors (such as omeprazole, esomeprazole, lansoprazole and pantoprazole); antidiabetic agents, such as sulfonylureas (for example, chlorpropamide, glipizide, glyburide, and glimepiride); and antihypertensives, such as alpha-adrenergic blockers, (for example, prazosin, doxazosin or terazosin), or beta blockers, (for example, acebutolol, atenolol, metoprolol, nadolol, pindolol and propanolol).

As discussed in the Background section hereinabove, weight gain associated with use of certain drugs may be due to, for example, food cravings, decreased exercise capacity, or stimulation of appetite, for example by blocking of histamine receptors. Involvement of $5-HT_{2A}$, $5-HT_{2C}$, $H_1$-histaminergic, and $M_1$-muscarinic receptors in weight gain has also been described.

In another embodiment, the method according to this aspect of the present invention, can be implemented to reduce weight gain associated with smoking cessation.

Weight gain associated with cessation of smoking may be attributed, for example, to the fact that nicotine increases heart rate and increases metabolism, such that readjustment to a lower metabolic rate is required once nicotine is no longer present in the bloodstream; to the fact that nicotine is an appetite suppressant; and to the need for emotional comfort in a subject suffering from the unpleasant symptoms associated with nicotine withdrawal.

Weight gain associated with cessation of smoking may also occur due to the use of drugs in this respect. Presently, there are a few drugs that are given in this respect. These include, for example, nicotine-replacement products, such as nicotine patches, nicotine gum (nicotine polacrilex), nicotine inhaler, and nicotine nasal spray, as well as the newer non-nicotine-based medications, such as Zyban™ (bupropion hydrochloride), and future therapies such as Cannabioind receptor affecting Acomplia™ (rimonabant). Administration of the $H_1$ agonist described herein can be effected in combination with any of these and other drugs for smoking cessation.

Weight gain also frequently occurs during a holiday season. This may be due to the fact that with greater leisure time at his disposal, a subject has more opportunity to eat more frequently, or because partaking of elaborate meals is often an integral part of a holiday celebration. This is exacerbated by holidays, particularly religious or national holidays, which are associated with festive meals, or consumption of particular kinds of food. These include, for example, the festive Thanksgiving meal, Christmas dinner, the Jewish Passover meal, and the like.

The $H_1$-receptor agonists described herein can be further efficiently used for improving a compliance of a human subject to caloric restriction. Thus, according to another aspect of the present invention, there is provided a method of improving a compliance of a human subject to caloric restriction, which is effected by administering to the subject a therapeutically effective amount of an $H_1$ agonist as described herein. The method, according to this aspect of the present invention can be beneficially practiced with human subject undergoing a weight reducing diet or any other caloric restriction.

By efficiently regulating food intake in human subjects and improving a compliance thereof to caloric restriction the methods described hereinabove may further be used for inducing weight loss, for maintaining weight loss after or during a weight reducing diet, or for inhibiting weight gain in a subject having a condition associated with weight gain. For inducing or maintaining weight loss, the $H_1$ receptor agonist of the present invention may optionally be administered in conjunction with other methods of treatment, such as diet, exercise, behavioral therapy, drug therapy, or surgical therapy.

The $H_1$-receptor agonists described herein can be further efficiently used for reducing a desire of a human subject to consume fats. Some neurotransmitters and neuromodulators have been shown to control both amount eaten and selection of food in a mancronutrient specific manner (Lecklin et al., 2002). For example, as is discussed hereinabove and is further demonstrated in FIGS. 1 and 2, metoprine has been shown to suppress daily ingestion of fats in rats, while having no effect on intakes of carbohydrates or proteins, indicating that an increase in the brain histamine content may specifically affect the desire to consume fats.

As is demonstrated in the Examples section that follows, it has been found that betahistine treatment resulted in a significant decrease in fat consumption in human subjects over a 28 day trial, while consumption of carbohydrates was not significantly altered. The increase in brain histamine caused by administration of the $H_1$-receptor agonists of the present invention may therefore be effective in reducing the desire of a human subject to consume fats.

Thus, according to still another aspect of the present invention, there is provided a method of reducing the desire of a human subject to consume fats, which is effected by administering to the subject a therapeutically effective amount of the $H_1$ agonist described herein.

The clinical finding that the $H_1$ agonist of the present invention reduces fat intake in humans is of unique importance, not only with regard to obese subjects, but also with regard to patients suffering from conditions that are associated with fat consumption and/or in which reduced fat consumption is beneficial.

Thus, according to a further aspect of the present invention, there is provided a method of treating a condition in which reduced fat consumption is beneficial, which is effected by administering to a subject in need thereof a therapeutically effective amount of an $H_1$ agonist, as described herein.

Reducing the fat consumption of a subject can be further utilized for treating conditions associated with metabolic derangement.

Thus, according to still another aspect of the present invention, there is provided a method of treating a condition associated with a metabolic derangement in a human subject, which is effected by administering to the subject a therapeutically effective amount of the $H_1$ agonist described herein.

Such conditions are typically associated with metabolic derangement and more particularly with adverse imbalance of metabolites such as total cholesterol, HDL-cholesterol, LDL-cholesterol, triglycerides and the like and include, for example, dyslipidemia, such as hypercholesterolemia or lipemia and diabetes.

Dyslipidemias are disorders of lipoprotein metabolism, including lipoprotein overproduction or deficiency. These disorders may be manifested by elevation of the serum total cholesterol, low-density lipoprotein (LDL) cholesterol and triglyceride concentrations, and a decrease in the high-density lipoprotein (HDL) cholesterol concentration and therefore include, for example, lipemia and hypercholesterolemia.

Lipemia is a condition in which an excess of fats or lipids is found in the blood of subject.

Hypercholesterolemia is a condition in which high levels of cholesterol are found in the blood of a subject.

A direct connection has been shown between coronary artery disease and dyslipidemia. Dyslipidemias may be genetic in origin, or may be due to dietary factors (such as excess saturated fats, "trans" fatty acids, cholesterol, excess calories, or alcohol) or drug use (including steroid hormones, diuretics, beta-blockers, cyclosporine and amiodarone, or olanzapine). Dyslipidemias may also be associated with hypothyroidism, diabetes mellitus, hepatobiliary obstruction, nephritic syndrome and chronic renal failure, or with systemic diseases such as porphyries, systemic lupus erythematosis, and lymphomas. The most commonly used options for pharmacologic treatment of dyslipidemia include fibrates, HMG-CoA reductase inhibitors (such as statins), bile acid sequestrants, cholesterol absorption inhibitors, nicotinic acid and derivatives thereof.

High cholesterol level, as well as other manifestations of dyslipidemia, can cause the formation and accumulation of plaque deposits in the arteries, leading to plaque ruptures and blockages in the arteries, which increase the risk for heart attack, stroke, circulation problems, and death. Patients suffering from metabolic derangement that is manifested by dyslipidemia are therefore typically instructed to follow a low fat diet as a first measure, before being prescribed drugs which affect cholesterol metabolism. However, patient compliance with these instructions is generally not high, and currently there are no available drugs for helping patients to adhere to such a diet. Therefore, the $H_1$ agonist of the present invention, in reducing the desire of a patient to consume fats, helps such patients to maintain a low fat diet.

Hence, according to still another aspect of the present invention, there is provided a method of reducing total cholesterol level in a human subject, which is effected by administering to the subject a therapeutically effective amount of the $H_1$ agonist described herein.

Total cholesterol consists of HDL cholesterol and LDL cholesterol. High density lipoprotein (HDL), commonly referred to as "good" cholesterol, tends to carry cholesterol away from the arteries and back to the liver, where it is passed from the body. It is also believed that HDL cholesterol removes excess cholesterol from plaque in arteries, thus slowing the buildup. An increase in HDL cholesterol is therefore considered beneficial. In contrast, LDL cholesterol is considered to be "bad" cholesterol, being responsible for plaque formation and deposits. Reducing LDL-cholesterol is believed to be responsible for reducing or stopping the formation of new cholesterol plaques on the artery walls; reducing existing cholesterol plaques on the artery walls; widening narrowed arteries; preventing the rupture of cholesterol plaques, which initiates blood clot formation; decreasing the risk of heart attacks; and decreasing the risk of strokes.

Thus, according to still another aspect of the present invention, there is provided a method of reducing low-density lipoprotein cholesterol and increasing high-density lipoprotein cholesterol levels in a human subject, which is effected by administering to the subject a therapeutically effective amount of the $H_1$ agonist described herein.

Triglycerides are common types of fats (lipids) that are essential for good health when present in normal amounts. They account for about 95 percent of the body's fatty tissue. Triglycerides are both present in food and manufactured by the body. Abnormally high triglyceride levels are associated with a number of diseases and conditions, such as cirrhosis, underactive thyroid, poorly controlled diabetes, and pancreatitis. High triglyceride levels are also associated with known risk factors for heart disease, such as low levels of HDL cholesterol, high levels of LDL cholesterol and obesity. Triglycerides may also contribute to atherosclerosis.

Hence, according to still another aspect of the present invention, there is provided a method of reducing triglyceride level in a human subject, which is effected by administering to the subject a therapeutically effective amount of the $H_1$ agonist described herein.

In any of the methods described herein, the $H_1$ agonist may optionally be administered together with a therapeutically effective amount of an additional active agent that may affect the condition being treated.

According to a preferred embodiment of the present invention, the additional active ingredient can be, for example, a weight control agent. Any of the presently known and approved weight control agents or related substances can be used according to this embodiment. Hence, representative examples of such active ingredients include, for example, lipase inhibitors. A non-limiting example of a lipase inhibitor suitable for co-administration with the $H_1$ agonist of the present invention is Orlistat, which acts by binding to gastrointestinal lipases in the lumen of the gut, preventing hydrolysis of dietary fat into absorbable free fatty acids and monoacylglycerols. Orlistat is currently the only FDA-approved medication for obesity that reduces nutrient absorption.

Additional examples of such active ingredients include Sibrutamine, an inhibitor of both norepinephrine reuptake and serotonin reuptake that also weakly inhibits dopamine reuptake, which is approved by the FDA for weight loss and weight maintenance in conjunction with a reduction diet. Additional examples of such active ingredients include amphetamines, although the administration thereof might be restricted to a limited time period. A non-limiting example of an amphetamine suitable for co-administration with the $H_1$ agonist of the present invention is Fentermine.

Additional examples of such active ingredients include canabinoid receptor antagonists. A non-limiting example of a canabinoid receptor antagonist suitable for co-administration with the $H_1$ agonist of the present invention is Rimonabant, a recently developed drug that is currently undergoing Phase III trials and which is claimed to stop food cravings.

Alternatively, the additional active agent may be an agent for the treatment of a musculoskeletal disorder, a cardiovascular disorder, a dermatological disorder, a sleep disorder, a metabolic condition, dyslipidemia (including hypercholesterolemia and lipemia), diabetes or a diabetes-related condition. Such agents are not necessarily associated with weight gain, but may be administered together with the $H_1$ agonist of the present invention, for treatment of additional conditions from which the subject may suffer.

Representative examples of agents for the treatment of musculoskeletal disorders include, without limitation, anti-inflammatory agents, including non-steroidal anti-inflammatory drugs, muscle relaxants, anti-gout agents (such as allopurinol, colchicine, and uricosuric drugs), immunosuppressants (such as glucocorticoids, gold, and cytotoxic agents) and drugs affecting bone mineralization (e.g., diphosphonates, calcitonin, estrogen analogs).

Representative examples of non-steroidal anti-inflammatory drugs include, without limitation, piroxicam, isoxicam, tenoxicam, sudoxicam, and CP-14,304; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone.

Non-limiting examples of steroidal anti-inflammatory drugs include, without limitation, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (flupred-nylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

Representative examples of agents for the treatment of cardiovascular disorder include, without limitation; angiotensin-converting enzyme inhibitors (such as captopril, enalapril, or lisinopril); antiarrhythmic drugs (such as amiodarone); anticoagulants, antiplatelets or thrombolytics (such as aspirin); centrally acting drugs (such as clonidine, guanfacine or methyldopa); digitalis drugs (such as digoxin); diuretics (such as chlorthalidone); nitrates (such as nitroglycerin); peripheral adrenergic antagonists (such as reserpine); and vasodilators (such as hydralazine).

Representative examples of agents for the treatment of sleep disorders include, without limitation, hypnotic medications, such as benzodiazepines (including flurazepam, estazolam, temazepam and triazolam); zaleplon and zolpidem; eszopiclone; antidepressants, such as trazodone, antihistamines (such as diphenhydramine products).

Representative examples of agents for the treatment of diabetes include, without limitation, a meglitinide (such as repaglinide or nateglinide), a biguanide (such as metformin), a thiazolidinedione (such as rosiglitazone, troglitazone or pioglitazone), and an alpha-glucosidase inhibitor (such as acarbose or meglitol) and insulin.

Non-limiting examples of agents for the treatment of dyslipidemia include agents that lower serum total cholesterol, low-density lipoprotein (LDL) cholesterol and triglyceride concentrations such as, for example, fibrates, HMG-CoA reductase inhibitors, bile acid sequestrants, cholesterol absorption inhibitors including triglyceride absorption inhibitors, cholesterol biosynthesis inhibitors, including triglycerides absorption inhibitors, nicotinic acid and any analogs, metabolites and derivatives thereof.

HMG-CoA reductase inhibitors (statins) are well known drugs that effectively reduce LDL-cholesterol levels by inhibiting the enzyme that regulates the rate of cholesterol production and increasing the clearance of LDL-cholesterol present in the blood by the liver. Representative examples of commonly prescribed statins include Atorvastatin, Fluvastatin, Lovastatin, Pravastatin and Simvastatin.

Proliferative Activated Receptor (PPAR) agonists, also known as fibrates, are fatty acid-activated members of the nuclear receptor superfamily that play important roles in lipid and glucose metabolism, and have been implicated in obesity-related metabolic diseases such as hyperlipidemia, insulin resistance, and coronary artery disease. Fibrates are generally effective in lowering elevated plasma triglycerides and cholesterol and act as PPAR agonists. The most pronounced effect of fibrates includes a decrease in plasma triglyceride-rich lipoproteins (TRLs). Levels of LDL cholesterol (LDL-C) generally decrease in individuals with elevated baseline plasma concentrations, and HDL cholesterol (HDL-C) levels are usually increased when baseline plasma concentrations are low. Non-limiting examples of commonly prescribed fibrates include bezafibrate, gemfibrozil and fenofibrate.

Representative examples of cholesterol absorption inhibitors include ezetimibe. Ezetimibe is the first of a new class of cholesterol absorption inhibitors that potently and selectively inhibits dietary and biliary cholesterol absorption at the brush border of the intestinal epithelium, without affecting the absorption of triglyceride or fat-soluble vitamins. Ezetimibe thus reduces overall cholesterol delivery to the liver, secondarily inducing increased expression of LDL receptors, resulting in an increased removal of LDL-C from the plasma.

Cholesterol absorption may also be affected by Cholesteryl Ester Transfer Protein (CETP) inhibitors, which play a major role in atherogenesis, by reducing cholesteryl ester accumulation within macrophages and the arterial wall, and thus reducing foam cell formation and affecting the cholesterol absorption. The most promising presently known CETP inhibitor is avisimibe.

Bile acid sequestrants are a class of cholesterol lowering drugs that help rid the body of cholesterol by depleting cholesterol levels in the body. Bile is released from the liver and aids in the emulsification of fats. Cholesterol is a major component of bile, and most of the cholesterol from bile is reabsorbed into the bloodstream in the small intestine. Bile acid sequestrants act at the level of the small intestine and function in binding to bile, thus preventing cholesterol from being reabsorbed into circulation. Instead, the medication and bile will form an insoluble complex and be excreted in the feces. Examples of commonly prescribed bile acid sequesterants include Cholestyramine (Questran®) and colestipol (Colestid®).

Representative examples of cholesterol biosynthesis inhibitors include squalene inhibitors (such as monooxygenase and synthase). Squalene is an isoprenoid compound structurally similar to beta-carotene, is an intermediate metabolite in the synthesis of cholesterol. In humans, about 60 percent of dietary squalene is absorbed. It is transported in serum generally in association with very low density lipoproteins and is distributed ubiquitously in human tissues, with the greatest concentration in the skin, where it is one of the major components of skin surface lipids. Squalene inhibitors (e.g., monooxygenase and synthase) serve as cholesterol biosynthesis inhibitors.

Nicotinic acid is a known agent that lowers total cholesterol, LDL-cholesterol, and triglyceride levels, while raising HDL-cholesterol levels. There are three types of nicotinic acid drugs: immediate release, timed release, and extended release. Nicotinic acid or niacin, the water-soluble B vitamin, improves all lipoproteins when given in doses well above the vitamin requirement.

Additional active agents that can be utilized according to this embodiment of the present invention include, for example, analgesics, growth factors and toxins.

Non-limiting examples of analgesics (pain relievers) include aspirin and other salicylates (such as choline or magnesium salicylate), ibuprofen, ketoprofen, naproxen sodium, and acetaminophen.

Growth factors are hormones which have numerous functions, including regulation of adhesion molecule production, altering cellular proliferation, increasing vascularization, enhancing collagen synthesis, regulating bone metabolism and altering migration of cells into given area. Non-limiting examples of growth factors include insulin-like growth factor-1 (IGF-1), transforming growth factor-β (TGF-β), a bone morphogenic protein (BMP) and the like.

Non-limiting examples of toxins include the cholera toxin, which also serves as an adjuvant.

When utilized in each of the methods and aspects described above, the $H_1$ agonist of the present invention optionally and preferably forms a part of a pharmaceutical composition. The pharmaceutical composition comprises, in addition to the $H_1$ agonist, a pharmaceutically acceptable carrier, and may optionally further comprise one or more components selected from binding agents, stabilizers, diluents, excipients, surfactants, flavors, and odorants.

As used herein a "pharmaceutical composition" refers to a preparation of one or more of the active ingredients described herein, either compounds or physiologically acceptable salts thereof, with other chemical components such as traditional drugs, physiologically suitable carriers and excipients. Thus, a pharmaceutical composition, according to the present embodiments, can include the $H_1$ agonist described herein, either as the sole active ingredient, or combined with any of the active ingredients described herein, including, for example, weight control agents, drugs that a treatment therewith is associated with weight gain (e.g., antipsychotics, antidepressants and the like), agents for the treatment of a musculoskeletal disorder, a cardiovascular disorder, a dermatological disorder, a sleep disorder, a metabolic condition, diabetes or a diabetes-related condition, and agents for treating dyslipidemia (including lipemia and hypercholesterolemia, e.g., cholesterol and/or triglycerides absorption inhibitors and cholesterol and/or triglycerides biosynthesis inhibitors), all as is detailed hereinabove.

Pharmaceutical compositions comprising one or more of the active ingredients described herein can therefore include, for example, the $H_1$ agonist described herein and an agent for treating dyslipidemia (e.g., cholesterol and/or triglyceride absorption inhibitor, cholesterol and/or triglyceride biosynthesis inhibitor, ezetimibe, orlistat, a cholesteryl ester transfer protein (CETP) inhibitor, a bile acid sequesterant, a fibrate, an HMG-CoA reductase inhibitor, a squalene inhibitor, nicotinic acid, a derivative, analog and metabolite thereof, and any mixture thereof, as is detailed hereinabove); the $H_1$ agonist described herein and a drug associated with weight gain (e.g., an antipsychotic, an antidepressant, a mood-stabilizer, a calcium channel blocker, an anti-convulsant, a proton pump inhibitor, an antidiabetic agent, an antihypertensive, a hormone, an anti-smoking medication and any combination thereof, as is detailed hereinabove); the $H_1$ agonists described herein and a weight control agent (e.g., Sibrutamine, Orlistat, Rimonabant, and more, as is detailed hereinabove); the $H_1$ agonist described herein and agent for treating diabetes, and the like.

The purpose of a pharmaceutical composition is to facilitate administration of an active ingredient (herein the $H_1$ agonist described above, optionally combined with other active ingredients) to an organism (herein, a human being). Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions.

Suitable pharmaceutical excipients include without limitation, calcium carbonate, calcium phosphate, various sugars and types of starch, cellulose derivatives, gelatin, vegetable oils, polyethylene glycols, sodium stearate, glycerol monostearate, talc, sodium chloride, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

Further techniques for formulation and administration of active ingredients may be found in "Remington's Pharmaceutical Sciences," Mack Publishing Co., Easton, Pa., latest edition, which is incorporated herein by reference as if fully set forth herein.

The pharmaceutical compositions herein described may also comprise suitable solid or gel phase carriers or excipients. Examples of such carriers or excipients include, but are not limited to, calcium carbonate, calcium phosphate, various sugars, starches, cellulose derivatives, gelatin and polymers such as polyethylene glycols.

Pharmaceutical compositions for use in accordance with the present invention thus may be formulated in conventional manner using one or more pharmaceutically acceptable carriers comprising excipients and auxiliaries, which facilitate processing of the active ingredients into preparations which, can be used pharmaceutically. Proper formulation is dependent upon the route of administration chosen.

Pharmaceutical compositions that comprise two or more active ingredient, as described hereinabove, can be formulated either as a single packaged pharmaceutical dose unit (further referred to herein as a "unitary dosage form") that includes the two or more active ingredients or as two or more separate units (e.g. two or more dosage forms) each including a single active ingredient and all preferably further packaged into a single delivery device (e.g., a capsule).

Since the $H_1$ agonist described herein is characterized by a desirable pharmacokinetic, reflected by a timed plasma peak concentration, the composition of the present invention is formulated such that the maximal efficacy of the active ingredients would provide an optimal effect with regard to the intended use of the combined composition.

Preferably, the composition of the present invention is formulated such that a plasma peak concentration of each of the active ingredients occurs substantially simultaneously. Thus, for example, compositions comprising one or more drugs associated with weight gain and the $H_1$ agonist described herein are formulated such that the plasma peak concentration of the $H_1$ agonist would occur within the time frame in which the plasma concentration of the drug causes appetite stimulation.

One approach for achieving the above, is to attenuate the release of the $H_1$ agonist with respect to the release of the other active ingredient(s) or, vice versa, attenuate the release of the other active ingredient(s) with respect to the release of the $H_1$ agonist. In order to achieve such staggered release, both agents may be in delayed release form of varying release profile, or one agent may be in immediate release form and the other agent(s) in delayed release form. In another approach, the agents are delivered as individual pulses, at spaced-apart time intervals.

An exemplary formulation includes capsules housing tablets or drug-containing beads or particles, a first portion of which comprises the $H_1$ agonist, and a second portion of which comprises another active ingredient, wherein each portion provides a different drug release profile. The capsule material may be either hard or soft, and as will be appreciated by those skilled in the art of pharmaceutical science, typically comprises a tasteless, easily administered and water soluble compound such as gelatin, starch or cellulose.

A unitary dosage form may comprise a single tablet with the first and second dosage units each representing an integral and discrete layer thereof. For example, drug-containing particles or drug-containing beads can be compressed together into a single tablet using conventional tableting means.

Delayed release may be achieved by any method known in the art. As will be appreciated by those skilled in the art, a number of methods are available for preparing drug-containing tablets or other dosage units which provide a variety of drug release profiles. Such methods include coating a drug or drug-containing composition, increasing the drug's particle size, placing the drug within a matrix, and forming complexes of the drug with a suitable complexing agent. Delayed release may be provided, for example, by coating a drug or a drug-containing composition with a selected membrane coating material, typically although not necessarily a polymeric material. Exemplary delayed release forms of $H_1$ agonist preparations are described hereinabove.

When a coating is used to provide delayed release dosage units, particularly preferred coating materials comprise bio-erodible, gradually hydrolyzable and/or gradually water-soluble polymers. The "coating weight," or relative amount of coating material per dosage unit, generally dictates the time interval between ingestion and drug release. Suitable membrane coating materials for effecting delayed release include, but are not limited to: cellulosic polymers such as hydroxypropyl cellulose, hydroxyethyl cellulose, hydroxypropyl methyl cellulose, methyl cellulose, ethyl cellulose, cellulose acetate, cellulose acetate phthalate, cellulose acetate trimellitate, hydroxypropylmethyl cellulose phthalate, cellulose ester-ether phthalate, hydroxypropylcellulose phthalate, alkali salts of cellulose acetate phthalate, alkaline earth salts of cellulose acetate phthalate, hydroxypropylmethyl cellulose hexahydrophthalate, cellulose acetate hexahydrophthalate, and carboxymethylcellulose sodium; acrylic acid polymers and copolymers preferably formed from acrylic acid, methacrylic acid, acrylic acid alkyl esters, methacrylic acid alkyl esters, and the like, e.g. copolymers of acrylic acid, methacrylic acid, methyl acrylate, ethyl acrylate, methyl methacrylate and/or ethyl methacrylate, vinyl polymers and copolymers such as polyvinyl pyrrolidone, polyvinyl acetate, polyvinylacetate phthalate, vinylacetate crotonic acid copolymer, and ethylene-vinyl acetate copolymers; and shellac, ammoniated shellac, shellac-acetyl alcohol, and shellac n-butyl stearate.

Alternatively, the delayed release dosage units, e.g, tablets or particles, may be formulated by dispersing the active ingredient within a matrix of a suitable material such as an insoluble plastic, a hydrophilic polymer, or a fatty compound. The insoluble plastic matrices may be comprised of, for example, polyvinyl chloride or polyethylene. Hydrophilic polymers useful for providing a matrix for a delayed release dosage unit include, but are not limited to, those described above as suitable coating materials. Fatty compounds for use as a matrix material include, but are not limited to, waxes generally (e.g., carnauba wax) and glyceryl tristearate. Once the active ingredient is mixed with the matrix material, the mixture can be compressed into tablets or processed into individual drug-containing particles.

Further examples of compositions in which one agent is delayed with respect to the other agent include a formulation in which one agent is provided in an outer, immediate release layer, which is released as a first pulse, while the other agent is contained within a core which is separated from the outer layer by a film layer of an enteric coating. The enteric coating slowly dissolves after the delivery of the first pulse of drug allowing the release of the second pulse.

Formulations for oral delivery can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should be suitable for the mode of administration.

For oral administration, the active ingredients can be formulated readily by combining the active ingredients with pharmaceutically acceptable carriers well known in the art. Such carriers enable the active ingredients of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active ingredient doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For transdermal administration, the composition can be formulated in a form of a gel, a cream, an ointment, a paste, a lotion, a milk, a suspension, an aerosol, a spray, a foam, a serum, a swab, a pledget, a pad or a patch. Formulations for transdermal delivery can typically include carriers such as water, liquid alcohols, liquid glycols, liquid polyalkylene glycols, liquid esters, liquid amides, liquid protein hydrolysates, liquid alkylated protein hydrolysates, liquid lanolin, lanolin derivatives, glycerin, mineral oil, silicone, petroleum jelly, lanolin, fatty acids, vegetable oils, parabens, waxes, and like materials commonly employed in topical compositions. Various additives, known to those skilled in the art, may be included in the transdermal formulations of the invention. For example, solvents may be used to solubilize certain active ingredients substances. Other optional additives include skin permeation enhancers, opacifiers, anti-oxidants, gelling agents, thickening agents, stabilizers, and the like.

For buccal administration, the compositions may take the form of tablets or lozenges formulated in conventional manner.

For administration by inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the active ingredient and a suitable powder base such as lactose or starch.

The active ingredients described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

The composition can be formulated as rectal compositions such as suppositories or retention enemas, using, e.g., conventional suppository bases such as cocoa butter or other glycerides.

The pharmaceutical compositions herein described may also comprise suitable solid of gel phase carriers or excipients. Examples of such carriers or excipients include, but are not limited to, calcium carbonate, calcium phosphate, various sugars, starches, cellulose derivatives, gelatin and polymers such as polyethylene glycols.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising the $H_1$ agonist of the invention, and optionally other active ingredients, formulated in a compatible pharmaceutical carrier may also be prepared, placed in an appropriate container, and labeled for treatment of an indicated condition, as is detailed herein.

Thus, for example, pharmaceutical compositions comprising the $H_1$ agonist of the invention and a drug that a treatment therewith is associated with weight gain (e.g., an antipsychotic), can be packaged in a packaging material and identified in print, in or on the packaging material, for use in the treatment of a condition for which the drug indicated, while reducing or preventing weight gain associated with this drug treatment, as is detailed hereinabove.

Pharmaceutical compositions comprising the $H_1$ agonist of the invention, a cholesterol and/or triglycerides absorption inhibitor and/or a cholesterol and/or triglycerides biosynthesis inhibitor can be packaged in a packaging material and identified in print, in or on the packaging material, for use in the treatment of a condition associated with metabolic derangement (e.g., dyslipidemia), as is detailed hereinabove.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following example, which together with the above descriptions, illustrate the invention in a non limiting fashion.

Example 1

The following study was conducted to evaluate the effect of oral administration of betahistine on food intake:

Twenty obese but otherwise healthy persons were recruited. Their characteristics upon recruitment are shown in Table 1. Exclusion criteria for the study were age younger than 18, active diseases, medication use, known hypersensitivity or contra-indication for the use of betahistine.

Each subject was randomly allocated to receive betahistine 16 mg at 10:00 and 16:00 or placebo. Weight, caloric intake (24 hour recall) and appetite during the day (VAS, Visual Analogue Score) were obtained on day 0, 14 and 28 of the study. Subjects were instructed to eat according to their appetite without limitations.

Statistical significance was assessed with t-test. BMI stands for body mass index.

TABLE 1

Patients' characteristics

| | Treatment | | |
|---|---|---|---|
| | betahistine | Placebo | |
| Age | 48 ± 9 | 38 ± 15 | NS |
| Weight (kg) | 93 ± 17 | 90 ± 4 | NS |
| BMI | 35.1 ± 7.3 | 32.7 ± 1.7 | NS |
| Mean caloric intake (kcal) | 975 ± 472 | 1397 ± 693 | NS |
| Mean appetite score (VAS) | 45 ± 15 | 50 ± 12 | NS |

NS denotes no statistical significance (p value > 0.05)

Of the 20 subjects recruited, 8 did not complete the study and were excluded from the final analysis:

Subject No. 3 (placebo) dropped out on day 3 due to side effects—weakness.

Subject No. 5 (betahistine) reported on day 5 food aversion that did not allow her to consume any food. She was instructed to reduce the dose by half and was excluded from the results analysis.

Subject No. 9 (placebo) was excluded for protocol violation.

Subject No. 11 (placebo) dropped out on week 4 due to flu.

Subject No. 13 (placebo) was lost to follow up.

Subject No. 15 (betahistine) dropped out on week 4 due to flu.

Subject No. 16 (placebo) dropped out on week 3 due to dyspnea.

Subject No. 17 (betahistine) was lost to follow up.

The effect of betahistine treatment on the total caloric intake, and on the specific consumption of fat, carbohydrates and protein of the participants in this study was also studied. The obtained data are presented in FIGS. 4 and 5.

As can be seen in FIG. 4, treatment with betahistine was found to reduce total caloric intake as compared to the placebo. The caloric intake decreased to 80 percents of the pre-treatment level at day 14 of treatment, and to 68 percents at day 28. No decrease was seen with the subjects receiving placebo.

As can be seen in FIG. 5, while only a small reduction in carbohydrate consumption occurred with betahistine treatment (6%), fat and protein consumption were reduced by 49% and 35%, respectively. At the same time patients treated with placebo increased their carbohydrates, fats and protein consumption by 24%, 3% and 37% respectively.

It is therefore clearly shown that betahistine significantly reduces the caloric intake and fat consumption of a human subject. Therefore, administration of betahistine may be efficiently utilized for both improving compliance of a human subject to caloric restriction, and for reducing the desire of a human subject to consume fat.

The effect of betahistine administration on weight change was also studied. The results are presented in FIG. 6. Four out of seven subjects in the treatment group lost more than 1 kg during the study period, in comparison to only one out of five in the placebo group.

These clinical data clearly show that betahistine is an efficient medication for weight management.

Example 2

In a further study, a healthy, overweight woman was treated twice daily with betahistine 16 mg for a month without any dietary changes. The level of certain metabolites of the woman, as observed in blood tests, was measured before and after the betahistine treatment and are presented in Table 2 below.

TABLE 2

| | Day 0 | Day 30 | Change |
|---|---|---|---|
| Total cholesterol | 167 | 155 | −7% |
| HDL-cholesterol | 54 | 58 | +7% |
| LDL-cholesterol | 99 | 84 | −15% |
| Triglycerides | 69 | 62 | −10% |
| Fructoseamine | 195 | 202 | +4% |

As seen in Table 2, the results show that during the 30-day time period studied, the total cholesterol level of the subject decreased, with a corresponding decrease in the level of LDL-cholesterol and an increase in the level of HDL-cholesterol. The level of triglycerides decreased, while the level of fructoseamine increased very slightly. It is therefore concluded that the subject restricted her fat intake, (as shown by the decrease in LDL-cholesterol), without reducing her carbohydrate intake, (as shown by the slight increase in fructosamine level), indicating that betahistine has a specific effect on reducing fat intake in a human subject.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

BIBLIOGRAPHY

Albera, R. et al. *Acta. Otolaryngol.* 123(5): 588-593 (2003).
Amelin, A. V. et al. *Zh. Nevrol. Psikhaitr. Im S.S. Korsakova* 103(5): 43-48 (2003).
Arrang, J.-M., et al. *Eur. J. Pharmacol.* 111: 73-84 (1985).
Attoub, S. *Life Sci.* 69: 469-78 (2001).
Babarich, N. C., et al. *J. Clin. Psychiatry* 65: 1480-1482 (2004).
Barrett, E., et al. *Diabetes Care* 27: 596-601 (2004).
Bjenning, C. *Int. Sendai Histamine Symp. P* 39-40 (2000).
Blandina, P. *Br. J. Pharmacol.* 119: 1656-64 (1996).
Boiko, A. N., et al. *Zh. Nevrol. Psikhaitr. Im S.S. Korsakova* 102(1): 42-45 (2002).
Botez, M. *Encephale* 1(3): 279-86 (1975).
Bustillo, J. R. et al. *Am. J. Psychiatryi* 153: 817-819 (1996).
Clapham, J. *Eur. J. Pharmacol.* 259: 107-14 (1994).
Clayman, C. B. *J. Amer. Med. Assoc.* 238:1289-1290 (1977).
Fossati, A. et al. *Pharmacol. Res.* 43389-392 (2001).
Fujino, A. et al. *Arch. Otolaryngol.* 120(5): 497-504 (1994).

Fukagawa, K. *Am. J. Physiol.* 256: R605-R611 (1989).
Goldstein, D. J. *Obes. Res.* 2: 92-98 (1993).
Gordon, C. R. et al. *J. Vestib. Res.* 13: 103-111 (2003).
Grahne, B., et al. *Med. Monatasschr.* 30(6); 273-275 (1976).
Gusev, E. et al. *Zh. Nevrol. Psikhaitr. Im S.S. Korsakova* 98: 19-21 (1998).
Hagan, M. M. *Peptides* 23: 377-382 (2002).
Imamura, M. *Circ. Res.* 78: 863-9 (1996).
Itoh, E., et al. *Biol. Psychiatry* 45: 475-481 (1999).
Kane, J. M. *Am. J. Psychiatry* 160: 290-296 (2003).
Koller, E., et al. *Am. J. Med* 111: 716-23 (2001).
Koller, E. (2002) *Pharmacotherapy* 22: 841-52
Krupnick J. G. et al., *Ann. Rev. Pharmacol. Toxicol.* 38: 289-319 (1998).
Lean, M. *Diabetes Care* 26: 1597-1605 (2003).
Lecklin, A. *Brain Res.* 793: 279-88 (1998).
Lecklin et al. *Inflamm. Res.* 51: suppl. 1, S53-S54 (2002)
Leurs, R. *Br. J. Pharmacol.* 116: 2315-21 (1995).
Leurs, R. *Trends Pharmacol. Sci.* 19: 177-84 (1998).
Lieberman, J. A. *Prim. Care Companion J. Clin. Psychiatry* 6: 8-13 (2004).
Lin, J. S. et al. *Brain Res.* 523: 325-30 (1990).
Machidori, H. *Brain Res.* 590: 180-6 (1992).
McMahon, F. G. *Arch. Intern. Med.* 160: 2185-91 (2000).
Malmo, K., et al. *Int. J. Obesity* 1-11 (2005).
Meyer, J. S., et al. *J. Clin. Pharmacol.* 14: 280-9 (1974).
Mitchell, J. E., et al. *Current Drug Targets* 2: 17-29 (2003).
Mokdad, A. H., *J. Amer. Med. Assoc.* 291: 1238-45 (2004).
Morimoto, T. *Behav. Brain Res.* 124: 145-150 (2001).
National Center for Health Statistics, Health E-Stats, Hyattsville, Md., (2000).
National Task Force on the Prevention and Treatment of Obesity, *J. Amer. Med. Assoc.* 276: 1907-15 (1996).
National Task Force on the Prevention and Treatment of Obesity, *Arch. Intern. Med.* 160: 898-904 (2000).
Odinak, M. M. et al. *Zh. Nevrol. Psikhaitr. Im S.S. Korsakova* 105(7): 55-57 (2005).
Onderwater, R. C. *Toxicology* 125: 117-29 (1998).
Physicians' Desk Reference, 55th edition, Montvale, N.J. (2001).
Pi-Sunyer et al. *American Heart Association (AHA) Scientific Sessions*, New Orleans, La. (2004).
Poyurovsky, M. et al. *Int. Clin. Psychopharmacol.* 20: 101-103 (2005).
Rasmussen, M. H. *Brit. Med. J.* 306: 1093-6 (1993).
Rossi, R., et al. *Physiol. and Behav.* 66: 517-521 (1999).
Sakata, T. *Obes. Res.* (Suppl. 4) S541-S548 (1995).
Sakata, T. *Nutrition* 13: 403-11 (1997).
Saljoughian et al., *U.S. Pharmacist*, 29: 2 (2004).
Seifert et al., *J. Pharmacol. Exp. Therap.* 305(3): 1104, 2003.
Seipel, J. H. et al. *J. Clin. Pharamacol.* 17: 140-161 (1977).
Serdula, M. K. *J. Amer. Med. Assoc.* 282: 1353-8 (1999).
Snyman, J. R., et al. *Immunopharmacology* 30(1): 71-8 (1995).
Stemoson, L. A. *Drug Metab. Dispos.* 2; 123-8 (1974).
Szelag, A., Malgorzata, T., and Merwid-Lad, A. *Polish J. Pharmacol.* 53: 701-707 (2001).
Szelag, A. *Adv. Clin. Exp. Med.* 11(3): 293-300 (2002).
Theisen, F. M., et al. *J. Neural Transm.* 110: 11-121 (2003).
Tuomisto, L. *Meth. Find. Exp. Clin. Pharmacol.* 16: 355-9 (1994).
Wadden, T. A. *Obes. Res.* 3: 549-57 (1995).
Wirshing, D. A. et al. *J. Clin. Psychiarty* 60: 358-363 (1999).
Wirshing, D. A. *J. Clin. Psychiatry* 65: 13-26 (2004).
Yoshimatsu, H. *Diabetes* 48: 2286-91 (1999).

What is claimed is:

1. A pharmaceutical composition comprising a therapeutically effective amount of betahistine or a salt thereof, and a therapeutically effective amount of olanzapine, the pharmaceutical composition being formulated for oral administration, wherein the dosage form is selected from the group consisting of a tablet, a pill, a dragee and a capsule.

2. The pharmaceutical composition of claim 1, being packaged in a packaging material and identified in print, in or on said packaging material, for use in the treatment of a medical condition in which treatment with olanzapine is beneficial while reducing weight gain associated with olanzapine.

3. The pharmaceutical composition of claim 1, wherein said betahistine salt is selected from the group consisting of betahistine dihydrochloride, betahistine mesilate, and betahistine trimebutine maleate.

4. The pharmaceutical composition of claim 1, wherein said therapeutically effective amount of said betahistine or salt thereof ranges from 2 mg per unit dosage to 96 mg per unit dosage.

5. The pharmaceutical composition of claim 1, being formulated such that said betahistine or salt thereof is in a slow-release form.

6. The pharmaceutical composition of claim 1, wherein said therapeutically effective amount of said betahistine or salt thereof ranges from 24 mg/day to 48 mg/day.

7. A pharmaceutical composition comprising a therapeutically effective amount of betahistine or a salt thereof, and a therapeutically effective amount of olanzapine, wherein said therapeutically effective amount of olanzapine is associated with a weight gain, and said therapeutically effective amount of betahistine or salt thereof is effective in reducing said weight gain, the pharmaceutical composition being formulated for oral administration, wherein the dosage form is selected from the group consisting of a tablet, a pill, a dragee and a capsule.

* * * * *

UNITED STATES PATENT AND TRADEMARK OFFICE
CERTIFICATE OF CORRECTION

PATENT NO. : 7,728,015 B2  
APPLICATION NO. : 11/363332  
DATED : June 1, 2010  
INVENTOR(S) : Nir Barak Page 1 of 1

It is certified that error appears in the above-identified patent and that said Letters Patent is hereby corrected as shown below:

Kindly amend in Column 9, Line 31 from "mitrazapine" to "mirtazapine"

Kindly amend in Column 24, Line 67 from "mitrazapine" to "mirtazapine"

Signed and Sealed this

Seventeenth Day of August, 2010

David J. Kappos
*Director of the United States Patent and Trademark Office*